United States Patent
Ota

(10) Patent No.: US 10,342,512 B2
(45) Date of Patent: Jul. 9, 2019

(54) ULTRASOUND DIAGNOSTIC IMAGING APPARATUS

(71) Applicant: KONICA MINOLTA, INC., Chiyoda-ku, Tokyo (JP)

(72) Inventor: Kazushi Ota, Hino (JP)

(73) Assignee: KONICA MINOLTA, INC., Tokyo (JP)

(*) Notice: Subject to any disclaimer, the term of this patent is extended or adjusted under 35 U.S.C. 154(b) by 375 days.

(21) Appl. No.: 14/167,750

(22) Filed: Jan. 29, 2014

(65) Prior Publication Data
US 2014/0221835 A1 Aug. 7, 2014

(30) Foreign Application Priority Data
Feb. 1, 2013 (JP) .................. 2013-018012

(51) Int. Cl.
*A61B 8/00* (2006.01)

(52) U.S. Cl.
CPC .............. *A61B 8/463* (2013.01); *A61B 8/465* (2013.01); *A61B 8/468* (2013.01); *A61B 8/469* (2013.01); *A61B 8/54* (2013.01); *A61B 8/44* (2013.01)

(58) Field of Classification Search
CPC .......... A61B 8/44; A61B 8/463; A61B 8/465; A61B 8/468; A61B 8/469; A61B 8/54
See application file for complete search history.

(56) References Cited

U.S. PATENT DOCUMENTS

| 6,951,543 B2 * | 10/2005 | Roundhill .............. A61B 8/465 600/443 |
| 8,517,946 B2 * | 8/2013 | Kim ........................ A61B 8/00 345/649 |
| 8,669,955 B2 | 3/2014 | Nishio et al. |

(Continued)

FOREIGN PATENT DOCUMENTS

| JP | 04241847 A | 8/1992 |
| JP | 2001-276062 A | 10/2001 |
| JP | 2007257220 A | 10/2007 |

(Continued)

OTHER PUBLICATIONS

Japanese Office Action (and English translation thereof) dated Jan. 19, 2016, issued in counterpart Japanese Application No. 2013-018012.

(Continued)

*Primary Examiner* — Michael T Rozanski
(74) *Attorney, Agent, or Firm* — Holtz, Holtz & Volek PC

(57) ABSTRACT

Disclosed is an ultrasound diagnostic imaging apparatus which displays an ultrasound image on a display screen of a display unit based on ultrasound image data. The ultrasound diagnostic imaging apparatus includes a touch panel and a control unit. The control unit is able to execute a vertical display mode to display two ultrasound images aligned vertically on the display screen and a horizontal display mode to display two ultrasound images aligned horizontally on the display screen. In each display mode, the control unit sets operation reception regions aligned vertically or horizontally on the touch panel. When the control unit detects an operation of touching one of the operation reception regions, the control unit sets an ultrasound image displayed in the touched side to a selected state.

10 Claims, 18 Drawing Sheets

(56) References Cited

U.S. PATENT DOCUMENTS

2014/0024939 A1    1/2014  Kato et al.
2014/0114190 A1*   4/2014  Chiang ................. G06F 3/0488
                                                          600/440

FOREIGN PATENT DOCUMENTS

| JP | 2007282794 A | 11/2007 |
|----|--------------|---------|
| JP | 4429635 B2   | 3/2010  |
| JP | 5134721 B1   | 1/2013  |
| WO | 2011013400 A1| 2/2011  |

OTHER PUBLICATIONS

Japanese Office Action (and English translation thereof) dated Sep. 6, 2016, issued in counterpart Japanese Application No. 2013-018012.

* cited by examiner

ULTRASOUND DIAGNOSTIC IMAGING APPARATUS

BACKGROUND

Field of the Invention

The present invention relates to an ultrasound diagnostic imaging apparatus.

Description of Related Art

Conventionally, there is known an ultrasound diagnostic imaging apparatus which is able to execute two modes where the modes are a single display mode in which one ultrasound image is displayed in an ultrasound image display region on a display screen of a display unit and a dual screen display mode in which the ultrasound image display region is divided in half vertically or horizontally, and two ultrasound images are displayed, one in each display region (for example, the above is described in Japanese Patent Application Laid-Open Publication No. 2001-276062).

When image adjustment, measurement, etc. are performed on the ultrasound image displayed in each display region in the dual screen display mode, it is useful to be able to perform the above operation for each display region. Therefore, it is necessary to switch by the user operation the display region (active) on which the image adjustment, measurement, etc. is performed.

Such various operation of conventional ultrasound diagnostic imaging apparatuses is performed by physically operating a user interface such as keys, trackball, rotary encoder and the like provided on an operation table (for example, Japanese Patent No. 4429635).

When the switch between the single display mode and the dual screen display mode or the image adjustment, measurement, etc. of the ultrasound image displayed in each display region of the dual screen display mode is performed using the physically operated user interface as shown in Japanese Patent No. 4429635, at least three keys are necessary to switch between the modes and to switch between the display regions in the dual screen display mode. However, the following problems occur when the ultrasound diagnostic imaging apparatus which is able to execute the dual screen display mode where the display region is divided between an upper display region and a lower display region, and the dual screen display mode where the display region is divided between a left display region and a right display region is configured to be operated by only three keys (for example, mode switching key: one, display region switching key: two). For example, when the active display region is switched in the dual screen display mode where the display region is divided between the upper display region and the lower display region, the keys positioned aligned in a left and right layout need to be operated, and operation cannot be done intuitively. In order to execute intuitive operation in such case, it is necessary to add the display region switching key for switching between upper and lower regions and many keys become necessary. As a result, space for positioning these keys are necessary on the operation table, and the size of the apparatus increases.

SUMMARY

The present invention has been made in consideration of the above problems, and it is one of main objects to provide an ultrasound diagnostic imaging apparatus where it is possible to operate the apparatus intuitively while achieving less consumption of space.

In order to achieve at least one of the above-described objects, according to an aspect of the present invention, there is provided an ultrasound diagnostic imaging apparatus which outputs a transmitting ultrasound to a test subject, obtains a receiving signal by receiving a reflecting ultrasound from the test subject, generates ultrasound image data based on the obtained receiving signal, and displays an ultrasound image on a display screen of a display unit based on the ultrasound image data, the ultrasound diagnostic imaging apparatus including:

a touch panel provided overlapped on the display screen of the display unit;

a control unit which is able to execute a vertical display mode to display two ultrasound images aligned vertically on the display screen of the display unit and a horizontal display mode to display two ultrasound images aligned horizontally on the display screen of the display unit, wherein in the vertical display mode, the control unit sets an upper side operation reception region and a lower side operation reception region aligned vertically on the touch panel, and when the control unit detects an operation of touching the upper side operation reception region, the control unit sets an ultrasound image displayed on an upper side to a selected state and when the control unit detects an operation of touching the lower side operation reception region, the control unit sets an ultrasound image displayed on a lower side to the selected state; and in the horizontal display mode, the control unit sets a left side operation reception region and a right side operation reception region aligned horizontally on the touch panel, and when the control unit detects an operation of touching the left side operation reception region, the control unit sets the ultrasound image displayed on a left side to the selected state, and when the control unit detects an operation of touching the right side operation reception region, the control unit sets the ultrasound image displayed on a right side to the selected state.

Preferably, in the ultrasound diagnostic imaging apparatus, the control unit is able to execute a single display mode to display one ultrasound image on the display screen of the display unit;

in the single display mode, the control unit displays a dual screen display mode advancing button in a predetermined region on the display screen of the display unit;

the control unit sets a dual screen display mode advancing button reception region on the touch panel corresponding to the display of the dual screen display mode advancing button;

when the control unit detects operation of touching the dual screen display mode advancing button reception region, the control unit advances the display mode from the single display mode to the vertical display mode or the horizontal display mode;

when the control unit advances the display mode to the vertical display mode, the control unit sets the upper side operation reception region and the lower side operation reception region in a region where the dual screen display mode advancing button reception region is set in the single display mode; and when the control unit advances the display mode to the horizontal display mode, the control unit sets the left side operation reception region and the right side operation reception region in a region where the dual screen display mode advancing button reception region is set in the single display mode.

Preferably, in the ultrasound diagnostic imaging apparatus, in the vertical display mode and the horizontal display mode, the control unit further sets a single display mode advancing button reception region in a region where the dual screen display mode advancing button reception region is set in the single display mode;

in the vertical display mode and the horizontal display mode, when the control unit detects operation of touching the single display mode advancing button reception region, the control unit advances the display mode from the vertical display mode or the horizontal display mode to the single display mode.

Preferably, in the ultrasound diagnostic imaging apparatus, in the vertical display mode, the control unit sets the upper side operation reception region and the lower side operation reception region corresponded to each display of two ultrasound images displayed aligned vertically; and in the horizontal display mode, the control unit sets the left side operation reception region and the right side reception region corresponded to each display of two ultrasound images displayed aligned horizontally.

Preferably, in the ultrasound diagnostic imaging apparatus, the control unit is able to execute a quadruple screen display mode to display four ultrasound images aligned in a matrix shape on the display screen of the display unit;

in the quadruple screen display mode, the control unit sets a first operation reception region, a second operation reception region, a third operation reception region, and a fourth operation reception region on the touch panel, the operation reception regions aligned in a matrix shape;

when the control unit detects operation of touching the first operation reception region, the control unit sets a first ultrasound image among the four ultrasound images to a selected state;

when the control unit detects operation of touching the second operation reception region, the control unit sets a second ultrasound image among the four ultrasound images to the selected state;

when the control unit detects operation of touching the third operation reception region, the control unit sets a third ultrasound image among the four ultrasound images to the selected state; and when the control unit detects operation of touching the fourth operation reception region, the control unit sets a fourth ultrasound image among the four ultrasound images to the selected state.

BRIEF DESCRIPTION OF THE DRAWINGS

The present invention will become more fully understood from the detailed description given hereinbelow and the appended drawings, and thus are not intended to define the limits of the present invention, and wherein.

DETAILED DESCRIPTION OF PREFERRED EMBODIMENTS

Figure 1:
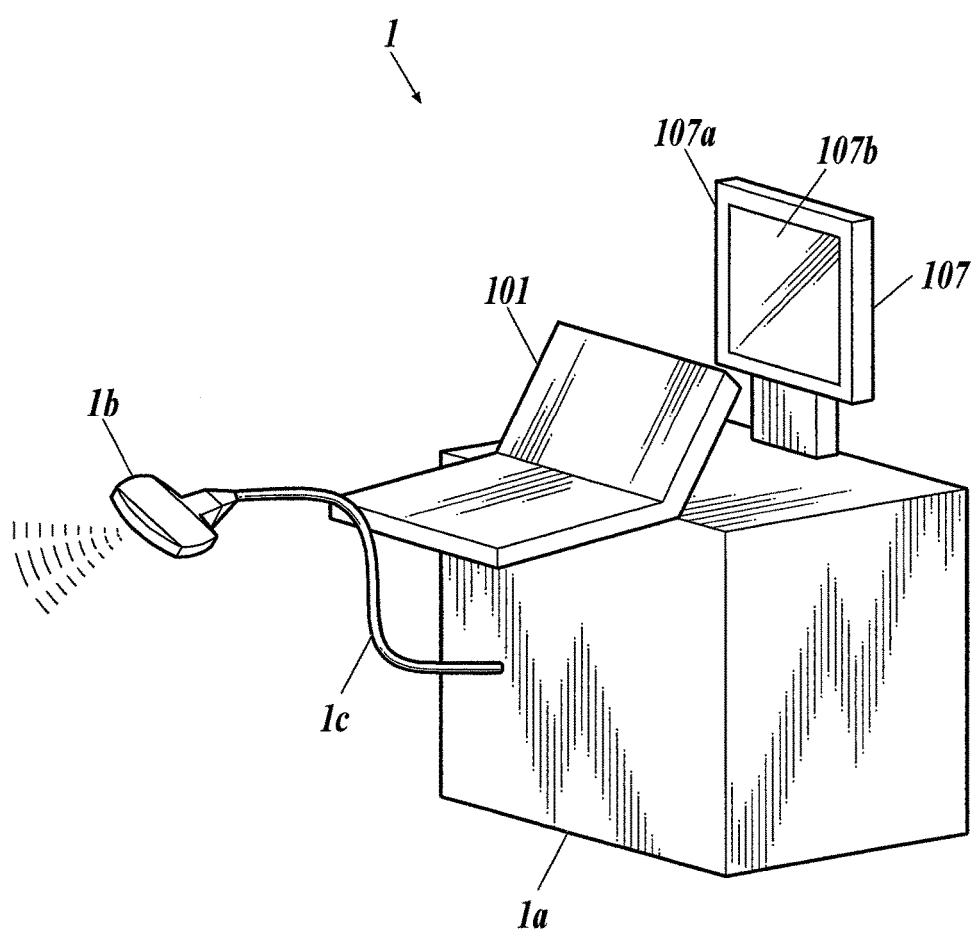
FIG. 1 is a diagram showing a configuration of an exterior appearance of an ultrasound diagnostic imaging apparatus.

Below, an embodiment of an ultrasound diagnostic imaging apparatus of the present invention is described with reference to the drawings. However, the present invention is not limited to the illustrated examples. In the description below, the elements with the same function and the same configuration are provided with the same reference numerals and the description is omitted.

First Embodiment

Figure 2:
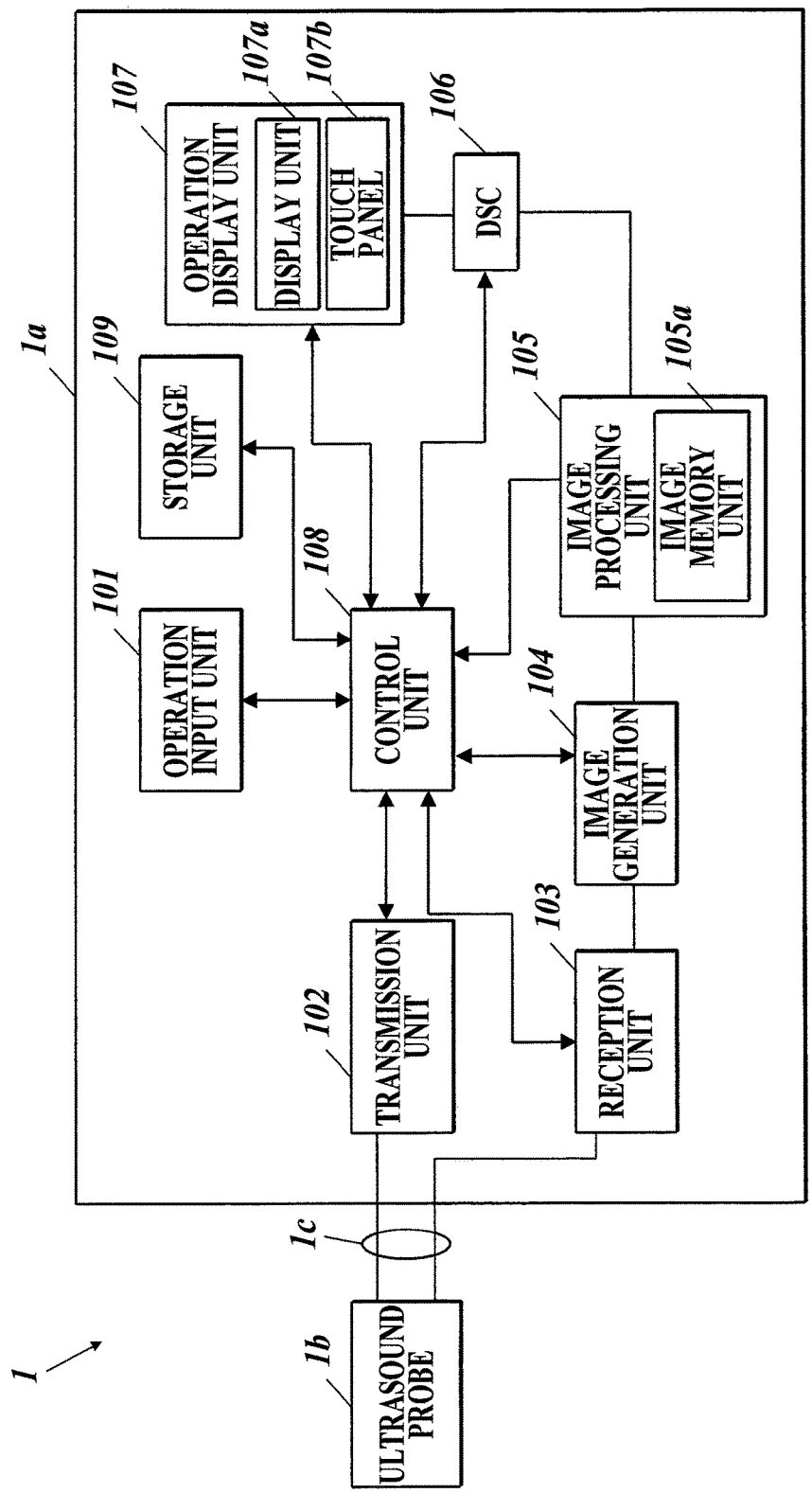
FIG. 2 is a block diagram showing a functional configuration of the ultrasound diagnostic imaging apparatus.

As shown in FIG. 1 and FIG. 2, the ultrasound diagnostic imaging apparatus 1 of the first embodiment includes an ultrasound diagnostic imaging apparatus main body 1a and an ultrasound probe 1b. The ultrasound probe 1b transmits ultrasound (transmitting ultrasound) to a test subject such as a live body which is not shown, and receives a reflecting sound (reflecting ultrasound: echo) of the ultrasound reflecting on the test subject. The ultrasound diagnostic imaging apparatus main body 1a is connected to the ultrasound probe 1b through a cable 1c. The ultrasound diagnostic imaging apparatus main body 1a transmits a driving signal which is an electric signal to the ultrasound probe 1b so that the ultrasound probe 1b transmits the transmitting ultrasound to the test subject. Then, the ultrasound diagnostic imaging apparatus main body 1a images an inner state of the test subject as an ultrasound image based on a receiving signal which is an electrical signal generated by the ultrasound probe 1b according to the reflecting ultrasound from the test subject received by the ultrasound probe 1b.

The ultrasound probe 1b is provided with an oscillator including piezoelectric elements, and for example, a plurality of oscillators are arranged in a one-dimensional array in an orientation direction. For example, the present embodiment uses the ultrasound probe 1b including 192 oscillators. The oscillators may be arranged in a two-dimensional array. The number of oscillators can be set freely. In the present embodiment, a linear scanning type electronic scanning probe is employed as the ultrasound probe 1b. However, either an electronic scanning type or a mechanical scanning type can be employed and any type among linear scanning type, sector scanning type or convex scanning type can be employed.

For example, as shown in FIG. 2, the ultrasound diagnostic imaging apparatus main body 1a includes, an operation input unit 101, a transmission unit 102, a reception unit 103, an image generation unit 104, an image processing unit 105, a Digital Scan Converter (DSC) 106, an operation display unit 107, a control unit 108, and a storage unit 109.

For example, the operation input unit 101 includes various switches, buttons, a trackball, a mouse, a keyboard, etc. to input a command to instruct start of diagnosis, data of personal information of the test subject and the like, and outputs operation signals to the control unit 108.

The transmission unit 102 is a circuit which supplies the driving signal which is the electric signal to the ultrasound probe 1b through the cable 1c so that the ultrasound probe 1b generates the transmitting ultrasound according to control by the control unit 108. For example, the transmission unit 102 includes a clock generating circuit, a delaying circuit, and a pulse generating circuit. The clock generating circuit is a circuit which generates a clock signal to determine the transmitting timing of the driving signal and the transmitting frequency. The delaying circuit is a circuit which sets the delaying time of transmitting the driving signal for each individual path corresponding to each oscillator and delays the transmitting of the driving signal in the amount of the set delaying time to focus the transmitting beam including the transmitting ultrasound. The pulse generating circuit is a circuit for generating the pulse signal as the driving signal at a predetermined cycle. For example, the transmission unit 102 configured as described above drives some of the consecutive oscillators (for example, 64 oscillators) among the plurality of oscillators (for example, 192 oscillators) arranged in the ultrasound probe 1b to generate the transmitting ultrasound. Each time the transmitting ultrasound is generated, the transmission unit 102 shifts the oscillators which are driven in the orientation direction to perform scanning.

The reception unit 103 is a circuit which receives the receiving signal which is the electric signal from the ultrasound probe 1b through the cable 1c according to control by the control unit 108. For example, the reception unit 103 includes an amplifier, an A/D converting circuit, and a phase adding circuit. The amplifier is a circuit for amplifying the receiving signal at a preset amplifying factor for each individual path corresponding to each oscillator. The A/D converting circuit is a circuit for A/D conversion of the amplified receiving signal. The phase adding circuit is a circuit which provides delaying time for each individual path corresponding to each oscillator on the received signal on which A/D conversion is performed to adjust the time phase, and adds the above (phase addition) to generate sound ray data.

The image generation unit 104 performs envelope detecting processing and logarithm amplification on the sound ray data from the reception unit 103, and adjusts the dynamic range and the gain to convert the luminance. With this, the image generation unit 104 generates the B-mode image data. In other words, the B-mode image data shows the intensity of the receiving signal by luminance. Other than the B-mode image data, the image generation unit 104 is able to generate A-mode image data, M-mode image data and image data of the Doppler method.

The image processing unit 105 is provided with an image memory unit 105a including a semiconductor memory such as a DRAM (Dynamic Random Access Memory). The image processing unit 105 stores the B-mode image data output from the image generation unit 104 in the unit of frames in the image memory unit 105a. The image data in the unit of frames may be called ultrasound image data or frame image data. The frame image data stored in the image memory unit 105a is transmitted to the DSC 106 according to control by the control unit 108.

The DSC 106 converts the frame image data received from the image processing unit 105 to an image signal according to the scanning method of a television signal and outputs the signal to the operation display unit 107.

The operation display unit 107 includes a display unit 107a and a touch panel 107b.

The display unit 107a can be a display apparatus such as an LCD (Liquid Crystal Display), a CRT (Cathode-Ray Tube) display, an organic EL (Electronic Luminescence) display, an inorganic EL display, a plasma display, and the like. The display unit 107a displays an image on the display screen according to the image signal output from the DSC 106.

The touch panel 107b is a touch panel of a pressure sensitive type (resistive film sensitive type) positioning transparent electrodes in a grid like shape on the display screen of the display unit 107a. The touch panel 107b detects the voltage value of the X-Y coordinate of the pressure point pressed with the finger on the screen, and outputs the detected position signal as the operation signal to the control unit 108. The touch panel is not limited to a pressure sensitive type, and the touch panel can be suitably selected from various types such as a capacitance type to be used in the apparatus.

For example, the control unit 108 includes a CPU (Central Processing Unit), a ROM (Read Only Memory), and a RAM (Random Access Memory). The control unit 108 reads various processing programs such as a system program stored in the ROM to be expanded in the RAM and centrally controls the operation of the units of the ultrasound diagnostic imaging apparatus 1 according to the expanded program.

The ROM includes a nonvolatile memory such as a semiconductor, and executes a system program corresponding to the ultrasound diagnostic imaging apparatus 1 and various processing programs which can be executed on the system program to perform processing such as later described image file generating processing, plural image control processing and the like. The ROM also stores various pieces of data such as a gamma table and the like. These programs are stored in a format of a program code readable by the computer, and the CPU sequentially executes the operation according to the program code.

The RAM forms a work area which temporarily stores the various programs executed by the CPU and the data regarding the program.

For example, the storage unit 109 is composed of a large capacity storage medium such as an HDD (Hard Disk Drive) and stores data such as ultrasound image data generated by the image processing unit 105.

Next, the image file generating processing executed by the control unit 108 of the ultrasound diagnostic imaging apparatus 1 configured as described above is described with reference to FIG. 3.

Figure 5:
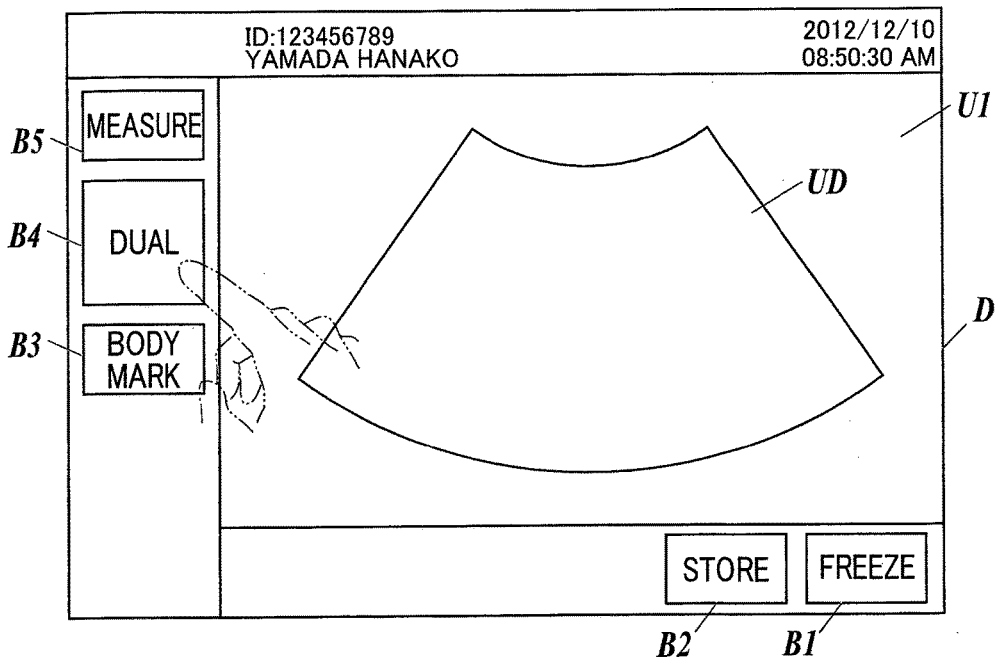
FIG. 5 is a diagram describing an example of an ultrasound image diagnostic screen.

First, when the personal information of the patient is input on the operation input unit 101 (step S101), the control unit 108 starts the scanning operation (step S102). In other words, the control unit 108 transmits and receives the ultrasound with the transmission unit 102 and the reception unit 103 and generates the ultrasound image data with the image generation unit 104 and the image processing unit 105. Then, the control unit 108 stores the generated ultrasound image data frame by frame in the image memory unit 105*a*. Here, setting of the ultrasound diagnostic modes such as a B-mode, a color Doppler mode, a pulse Doppler mode, an M-mode, etc. can be set. In the present embodiment, setting of a display format in a later described dual display mode can be set. In the present embodiment, the dual display mode includes a dual screen display mode and a quadruple screen display mode. The dual screen display mode includes a horizontal display mode which displays two ultrasound images aligned horizontally, and a vertical display mode which displays two ultrasound images aligned vertically. The quadruple screen display mode is a display mode which displays four ultrasound images aligned in a matrix of 2×2. Then, based on the ultrasound image data stored in the image memory unit 105*a*, for example, the control unit 108 displays on the display screen of the display unit 107*a* an ultrasound diagnostic screen D in which an ultrasound image UD is displayed in an ultrasound image display region U1 as shown in FIG. 5. The control unit 108 repeats the above operation parallel in later processing.

Figure 4:
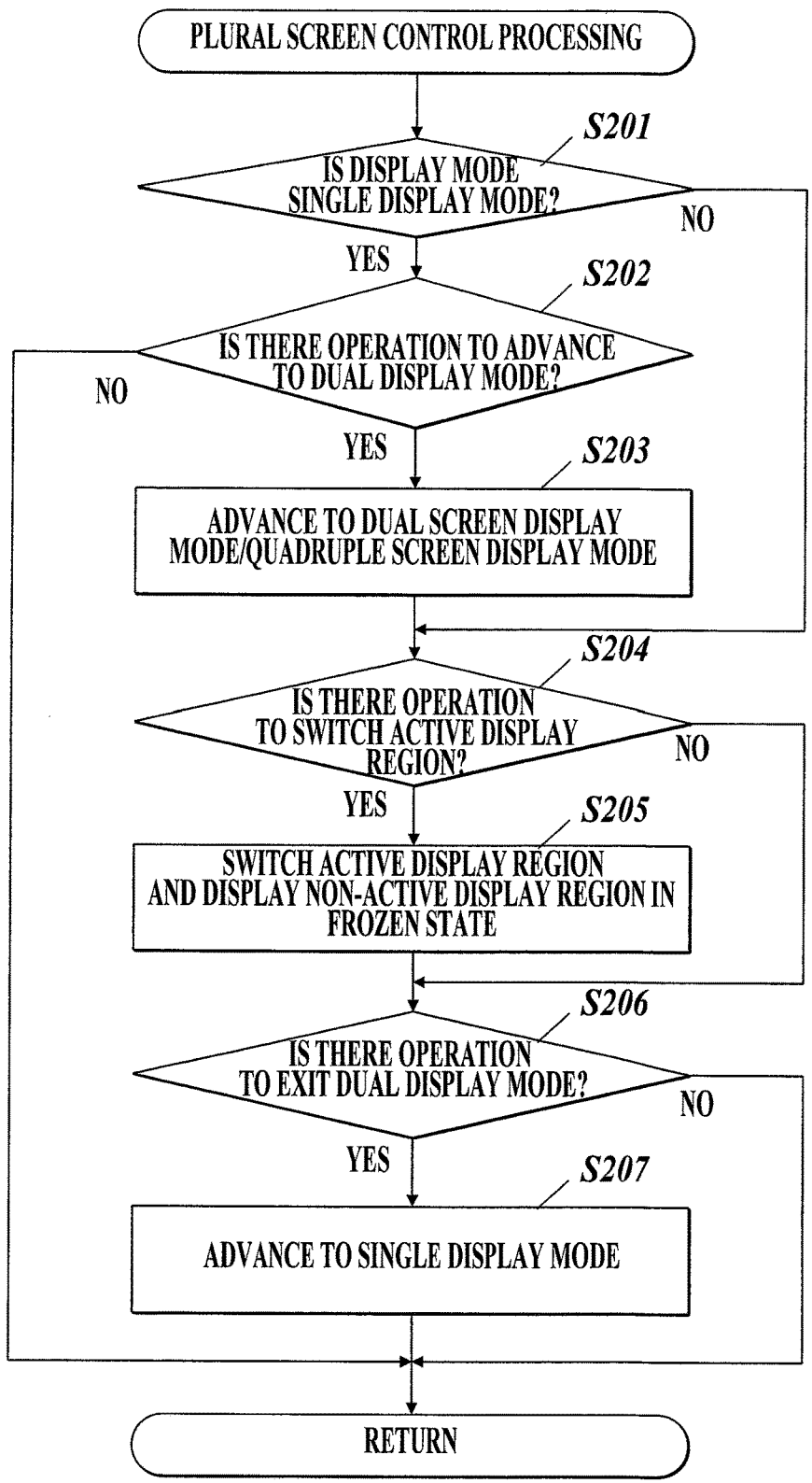
FIG. 4 is a flowchart describing the plural screen control processing.

Next, the control unit 108 performs the plural screen control processing (step S103). In the plural screen control processing, the mode is switched between the single display mode and the dual display mode, and the display region which is active in the dual display mode is switched. Here, the plural screen control processing is described with reference to FIG. 4.

First, the control unit 108 judges whether the present display mode is the single display mode which displays one ultrasound image on the display screen (step S201). When the control unit 108 judges that the present display mode is the single display mode (step S201: Y), the control unit 108 judges whether there is operation to advance to the dual display mode (step S202). As described below, the control unit 108 judges whether there is operation to advance to the dual display mode by whether operation of touching the dual display mode advancing button displayed on the display screen is received.

When the control unit 108 judges there is operation to advance to the dual display mode (step S202: Y), the display screen advances to the dual display mode in the display format set as described above (step S203). In other words, the control unit 108 advances the display mode so that the display format of the single display mode changes to the display format of the horizontal display mode, the vertical display mode or the quadruple screen display mode according to the above setting. Alternatively, when the control unit 108 does not judge that there is an operation to advance to the dual display mode (step S202; N), the processing ends.

In step S201, when the control unit 108 does not judge that the present display mode is the single display mode, in other words, when the control unit 108 judges that the present display mode is the dual display mode. (step S201: N), the control unit 108 performs the processing of step S204 without performing the processing of step S202 and step S203.

Next, the control unit 108 judges whether there is operation to switch the active display region (step S204). Specifically, in the horizontal display mode, an L button which allows the ultrasound image displayed on the left side to become active and an R button which allows the ultrasound image displayed on the right side to become active is displayed in a predetermined display region on the display screen. In the horizontal display mode, the control unit 108 receives operation of touching the L button and the R button so as to be able to judge the operation of switching the active display region. Alternatively, in the vertical display mode, a U button which allows the ultrasound image displayed on the upper side to become active and a D button which allows the ultrasound image displayed on the lower side to become active is displayed in a predetermined display region on the display screen. In the vertical display mode, the control unit 108 receives operation of touching the U button and the D button so as to be able to judge the operation of switching the active display region. Further, in the quadruple screen display mode, the following buttons are displayed in a predetermined display region on the display screen, a first button which allows the ultrasound image displayed in a first display region to become active, a second button which allows the ultrasound image displayed in a second display region to become active, a third button which allows the ultrasound image displayed in a third display region to become active, and a fourth button which allows the ultrasound image displayed in a fourth display region to become active. In the quadruple screen display mode, the control unit 108 receives operation of touching the first button to the fourth button so as to be able to judge the operation of switching the active display region.

When the control unit 108 judges there is operation to switch the active display region (step S204: Y), the control unit 108 switches the active display region to the display region corresponding to the operated button, and the ultrasound image displayed in the non-active display region which is not active is displayed fixed in a frozen state (step S205). Alternatively, when the control unit 108 does not judge that there is an operation to switch the active display region (step S204: N), the control unit 108 does not perform the processing of step S205 and performs the processing of step S206.

The control unit 108 judges whether there is operation to exit the dual display mode (step S206). As described below, the control unit 108 judges whether there is operation to exit the dual display mode by whether operation of touching the dual display mode exit button displayed on the display screen in the dual display mode is received.

When the control unit 108 judges there is operation to exit the dual display mode (step S206: Y), the display screen advances from the dual display mode to the single display mode (step S207). In other words, the control unit 108 advances the display mode so that the display format of the dual display mode changes to the display format of the single display mode. After performing the processing of step S207, the control unit 108 ends this processing. Alternatively, when the control unit 108 does not judge that there is operation to exit the dual display mode (step S206: N), the control unit 108 ends the processing without performing the processing of step S207.

Figure 3:
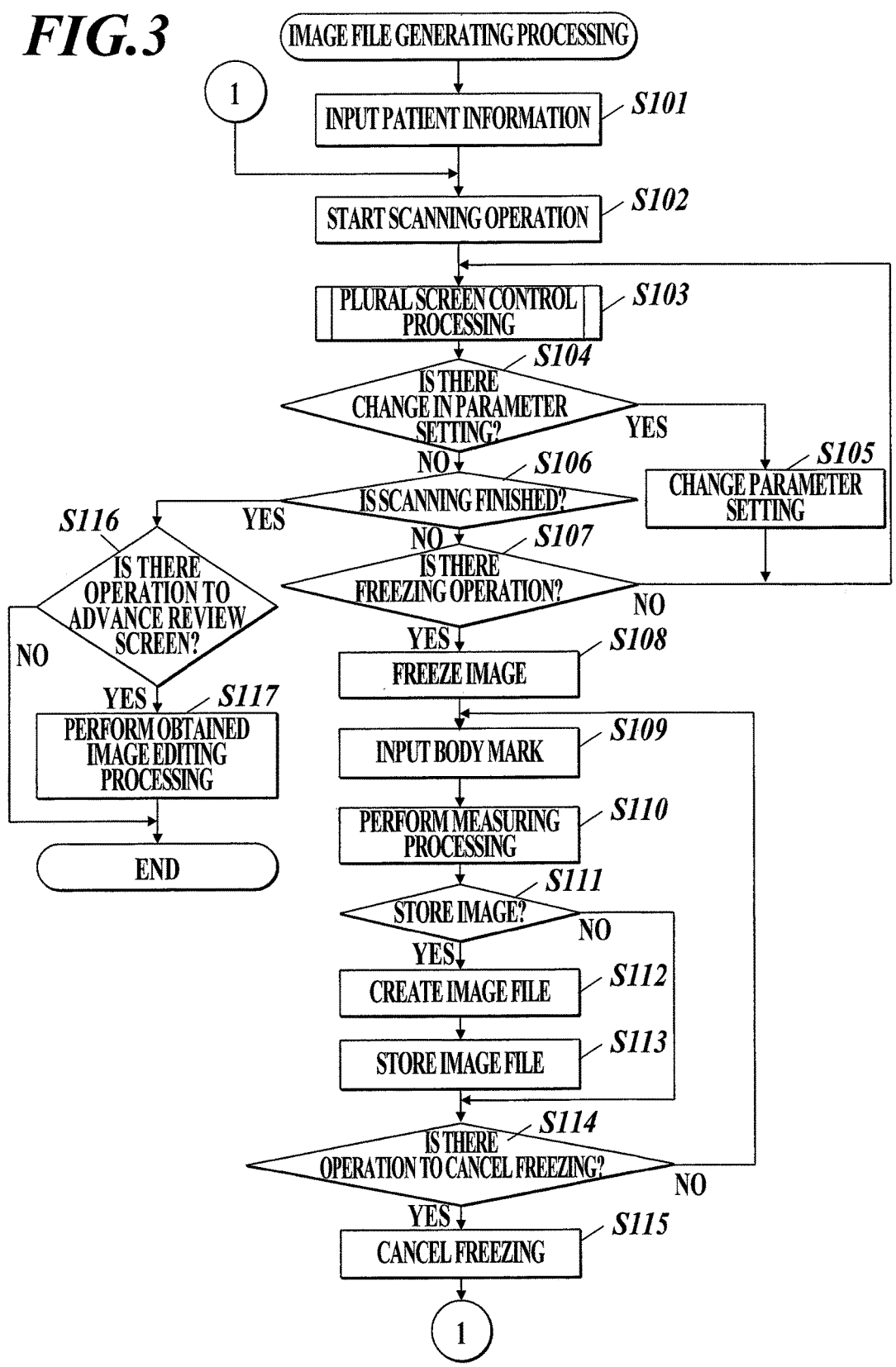
FIG. 3 is a flowchart describing the image file generating processing.

As shown in FIG. 3, when the plural screen control processing ends, the control unit 108 judges whether there is operation to change the setting of the various parameters described above on the operation input unit 101 or the operation display unit 107 (step S104).

When the control unit 108 judges that there is operation to change the setting of the parameter (step S104: Y), after performing the change of the setting of the parameter according to the input on the operation input unit 101 and the operation display unit 107 (step S105), the control unit 108 performs processing of step S103. For example, the parameter is display depth, gain and the like. The control unit 108 stores the parameter after changing the setting in the RAM, for example. In the dual display mode, the setting of the parameter of the ultrasound image in the active display region is changed.

Alternatively, in step S104, when the control unit 108 does not judge that there is operation to change the setting of the parameter (step S104: N), the control unit 108 judges whether to end the scanning operation (step S106). In other words, the control unit 108 judges whether operation on the operation input unit 101 to end one examination is received. The control unit 108 can judge that the operation to end is received by predetermined operation to end the examination or when information of another patient is set.

When the control unit 108 does not judge that the scanning operation ends (step S106: N), the control unit 108 judges whether there is operation to freeze the image on the operation input unit 101 and the operation display unit 107 (step S107). In other words, the control unit 108 judges whether there is operation to switch an ultrasound image displayed as a moving image on the display unit 107*a* to a still image. For example, as shown in FIG. 5, the operation to freeze the image can be performed by operation of touching the freeze button B1 when the ultrasound image is displayed as a moving image.

When the control unit 108 does not judge that there is operation to freeze the image (step S107: N), the control unit 108 performs the processing of step S103. When the control unit 108 judges that there is operation to freeze the image (step S107: Y), the control unit 108 performs control to freeze the image which is to fix the display of the ultrasound image displayed on the display unit 107*a* when the operation to freeze the image is received (step S108). In the present embodiment, when the image is frozen, the scanning operation is stopped. However, the ultrasound image can be displayed fixed on the display screen parallel to performing the scanning operation. In the dual display mode, the ultrasound image in the active display region is displayed fixed to freeze the image.

Next, the control unit 108 receives input of a body mark (step S109). For example, as shown in FIG. 5, the control unit 108 controls the state so as to be able to receive input of selection of the body mark by receiving the operation of touching the body mark button B3 displayed on the display unit 107*a*. Here, the control unit 108 displays the body mark list in the predetermined display region of the display unit 107*a* so that the user is able to input selection of the body mark. For example, the input of the selection of the body mark can be performed by operation of touching the desired body mark in the body mark list displayed on the display unit 107*a*. The body mark is an image combined with the ultrasound image for visually specifying the site to be examined. Other than a shape, the body mark may be a character, a symbol or the like, and may be any format as long as a user interpreting the image can identify the site to be examined by sight. When the control unit 108 receives input of the selection of the body mark as described above, the selected body mark is overlapped and displayed on the ultrasound image displayed fixed. Specifically, the control unit 108 combines the body mark image data with the ultrasound image data so that the body mark is overlapped and displayed in a predetermined position of the ultrasound image. The control unit 108 displays the ultrasound image on the display unit 107*a* based on the ultrasound image data combined as described above. Together with the body mark or instead of the body mark, a comment input on the operation input unit 101, etc. can be imaged to be combined with the ultrasound image. Other than specifying the site to be examined, the body mark can be used to specify a direction of the ultrasound probe when the ultrasound image data is obtained or the position when the ultrasound image data is obtained.

Next, the control unit 108 performs measuring processing (step S110). For example, as shown in FIG. 5, the measuring processing is performed when the control unit 108 receives operation of touching the measure button B5 displayed on the display unit 107*a*. For example, in the measuring processing, the control unit 108 receives input of two points of start and end as described later, calculates a distance between the two points, and displays the result.

Next, the control unit 108 judges whether there is image storing operation (step S111). Specifically, for example, as shown in FIG. 5, the control unit 108 judges whether there is operation to store the image by determining whether there is operation to touch the store button B2 displayed on the display unit 107*a*.

When the control unit 108 judges that there is operation to store the image (step S111: Y), the control unit 108 creates the image file based on the ultrasound image data combined with the body mark image data as described above (step S112). In other words, first, the control unit 108 reads the combined ultrasound image data from the image memory unit 105*a*. The control unit 108 converts the read ultrasound image data to image data for storing. The converted image data is, for example, a bitmap image. The converted image data can be compressed by a compression method such as JPEG (Joint Photographic Experts Group format).

When the body mark is not set, an image file is created based on ultrasound image data on which the body mark image data is not combined. Then, the control unit 108 adds additional information to the image data converted as described above to generate an image file including DICOM image data.

The control unit 108 stores the image file created as described above in the storage unit 109 (step S113).

Alternatively, in step S111, when the control unit 108 does not judge that there is operation to store the image (step S111: N), the control unit 108 performs the processing of step S114 without performing the processing of step S112 and step S113.

Then, the control unit 108 judges whether there is operation to cancel the freezing of the image (step S114). Specifically, the control unit 108 judges whether there is operation to cancel the freezing by determining whether there is operation to touch the freeze button B1 while the image is frozen.

When the control unit 108 judges that there is operation to cancel the freezing (step S114: Y), the control unit 108 cancels the freezing to switch the display of the ultrasound image on the display unit 107a from the fixed display to the display of the moving image (step S115), and performs the processing of step S102. Alternatively, when the control unit 108 does not judge that there is operation to cancel the freezing of the image (step S114: N), the control unit performs the processing of step S109.

After generating the image file as described above, when the control unit 108 judges the scanning operation ends in step S106 (step S106: Y), the control unit 108 judges whether there is operation to advance to the review screen (step S116). For example, the display is advanced to the review screen by receiving input of the predetermined button on the operation input unit 101.

When the control unit 108 judges there is operation to advance to the review screen (step S116: Y), after performing the obtained image editing processing (step S117), the control unit 108 ends the processing. Although described in detail later, in the obtained image editing processing, the control unit 108 displays as a list of thumbnail images on the display unit 107a the ultrasound image based on the ultrasound image data for the examined patient stored as described above. The control unit 108 edits the stored ultrasound image data according to operation of input on the operation input unit 101 and touch panel 107b. For example, when the ultrasound image data is edited, it is possible to erase the stored ultrasound image data from the storage unit 109. Alternatively, when the control unit 108 does not judge that there is operation to advance to the review screen (step S116: N), the control unit 108 ends the processing without performing the processing of step S117.

Next, described below is the transition of the display screen on the display unit 107a of the ultrasound diagnostic imaging apparatus 1 configured as described above.

When the scanning operation as described above is started, an ultrasound diagnostic screen D as shown in FIG. 5 is displayed on the display screen of the display unit 107a. An ultrasound image display region U1 positioned in the ultrasound diagnostic screen D, and the ultrasound image UD based on the ultrasound image data stored in the image memory unit 105a is displayed in the ultrasound image display region U1. On the lower side of the ultrasound image display region U1, the above described freeze button B1 and store button B2 are displayed, and on the left side of the ultrasound image display region U1, the body mark button B3, the dual display mode advancing button (dual screen display mode advancing button) B4 for advancing to the dual screen display mode and the quadruple screen display mode and the measure button B5 are displayed. Each position where the buttons B1 to B5 are displayed is set with a touch operation reception region, and when operation of touching the touch operation reception region corresponding to each button B1 to B5 is received, processing corresponding to the touched button B1 to B5 is performed. For example, a dual display mode advancing button reception region as the touch operation reception region is set in the position where the dual display mode advancing button B4 is displayed, and when operation of touching the dual display mode advancing button reception region is received, the display format advances to the dual screen display mode or the quadruple screen display mode in the display format set in advance as described above.

Figure 6:
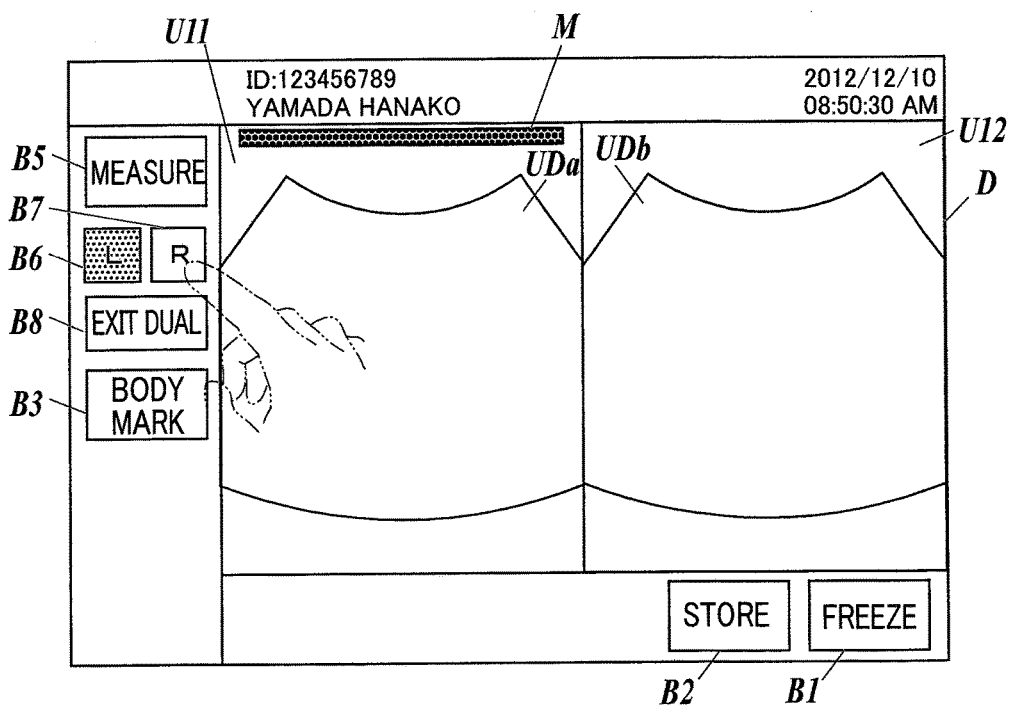
FIG. 6 is a diagram describing an example of an ultrasound image diagnostic screen.
Figure 7:
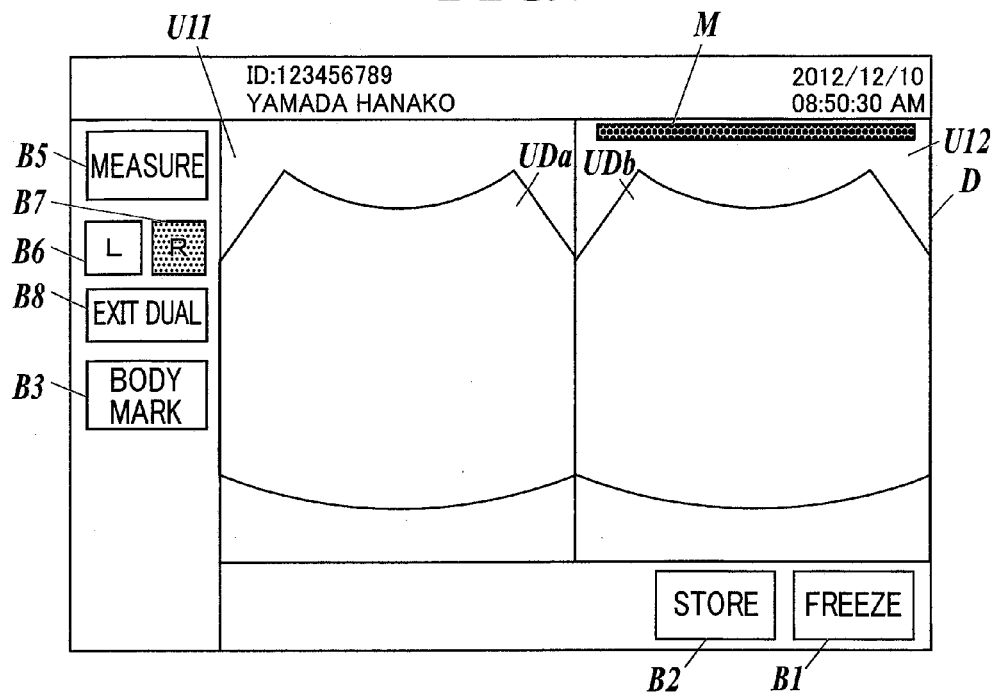
FIG. 7 is a diagram describing an example of an ultrasound image diagnostic screen.

For example, in a case where the dual display mode is set as advancing to the horizontal display mode of the dual screen display mode, when the operation of touching the dual display mode advancing button reception region is received, as shown in FIG. 6, the ultrasound image display region U1 is divided in half between left and right, and the display format is changed so that the left side display region U11 and the right side display region U12 are provided. Ultrasound images UDa and UDb are displayed respectively in the left side display region U11 and the right side display region U12. In the display region where the dual display mode advancing button B4 is displayed, instead of the button, an L button B6 and an R button B7 are displayed aligned horizontally on the upper side and a dual display mode exit button B8 is displayed below the above buttons. In the horizontal display mode, either one of the left side display region U11 or the right side display region U12 is active (selected state). An active mark M is displayed near the upper edge of the active display region of either the left side display region U11 or the right side display region U12. The user is able to acknowledge the active display region by confirming the display position of the active mark M. For example, the moving image of the ultrasound image is displayed in the active display region and the ultrasound image is displayed fixed in the display region which is not active (non-active display region). The left side operation reception region is set in the position where the L button B6 is displayed and the right side operation reception region is set in the position where the R button B7 is displayed. When the operation of touching each operation reception region is received, the active display region is switched. In other words, when the L button B6 is touched, the left side display region U11 becomes active, and when the R button B7 is touched, the right side display region U12 becomes active. For example, as shown in FIG. 6, when the left side display region U11 is active and the R button B7 is touched, as shown in FIG. 7, the right side display region U12 becomes active. A single display mode advancing button reception region is set in the position where the dual display mode exit button B8 is displayed. When the single display mode advancing button reception region is touched, the display format advances to the single display mode, and the ultrasound diagnostic screen D as shown in FIG. 5 is displayed on the display screen of the display unit 107a.

Figure 8:
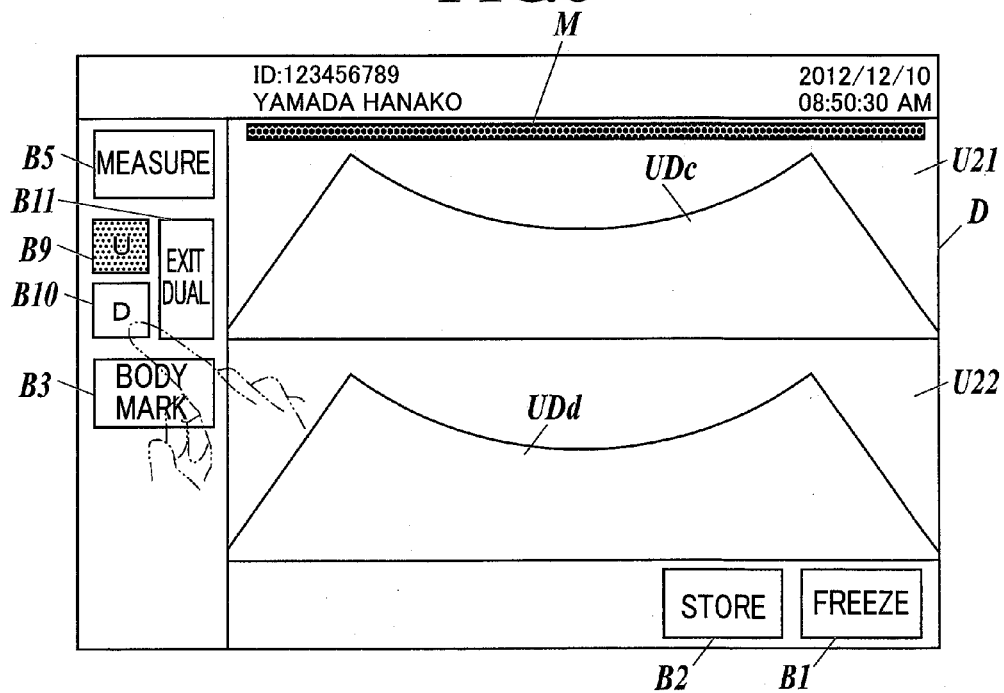
FIG. 8 is a diagram describing an example of an ultrasound image diagnostic screen.
Figure 9:
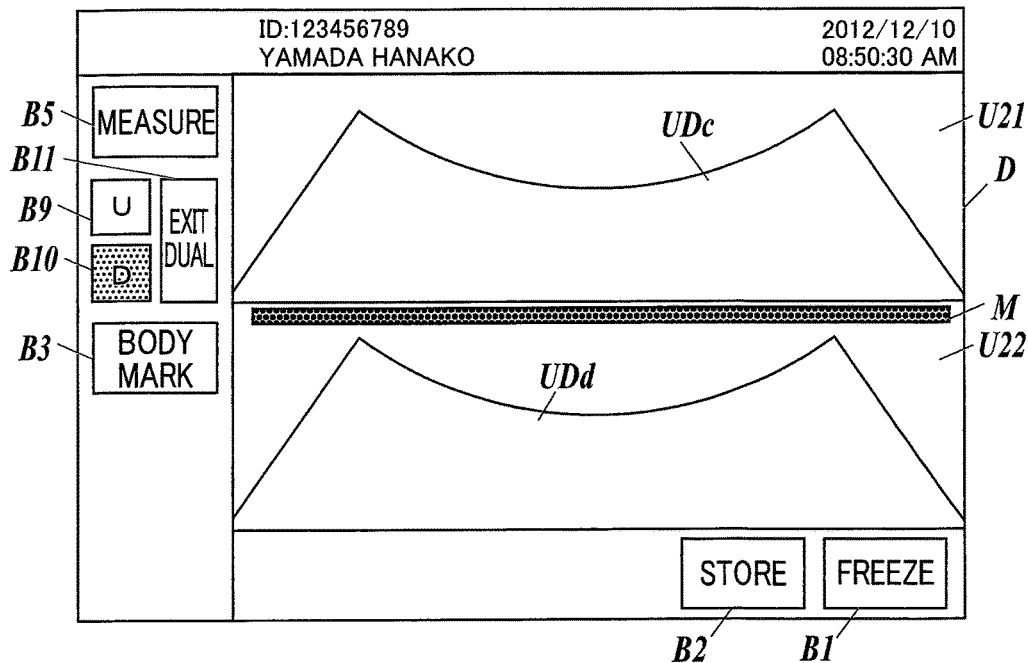
FIG. 9 is a diagram describing an example of an ultrasound image diagnostic screen.

Alternatively, in a case where the dual display mode is set as advancing to the vertical display mode of the dual screen display mode, when the operation of touching the dual display mode advancing button reception region is received, as shown in FIG. 8, the ultrasound image display region U1 is divided in half between the upper side and the lower side, and the display format is changed so that the upper side display region U21 and the lower side display region U22 are provided. Ultrasound images UDc and UDd are displayed respectively in the upper side display region U21 and the lower side display region U22. In the display region where the dual display mode advancing button B4 is displayed, instead of the button, a U button B9 and a D button B10 are displayed aligned vertically on the left side and a dual display mode exit button B11 is displayed on the right side of the above buttons. In the vertical display mode, either one of the upper side display region U21 or the lower side display region U22 is active. An active mark M is displayed near the upper edge of the active display region of either the upper side display region U21 or the lower side display region U22. The upper side operation reception region is set in the position where the U button B9 is displayed and the lower side operation reception region is set in the position where the D button B10 is displayed. When the operation of touching each operation reception region is received, the active display region is switched. In other words, when the U button B9 is touched, the upper side display region U21 becomes active, and when the D button B10 is touched, the lower side display region U22 becomes active. For example, as shown in FIG. 8, when the upper side display region U21 is active and the D button B10 is touched, as shown in FIG. 9, the lower side display region U22 becomes active. A single display mode advancing button reception region is set in the position where the dual display mode exit button B11 is displayed. When the single display mode advancing button reception region is touched, the display format advances to the single display mode as described above.

Figure 10:
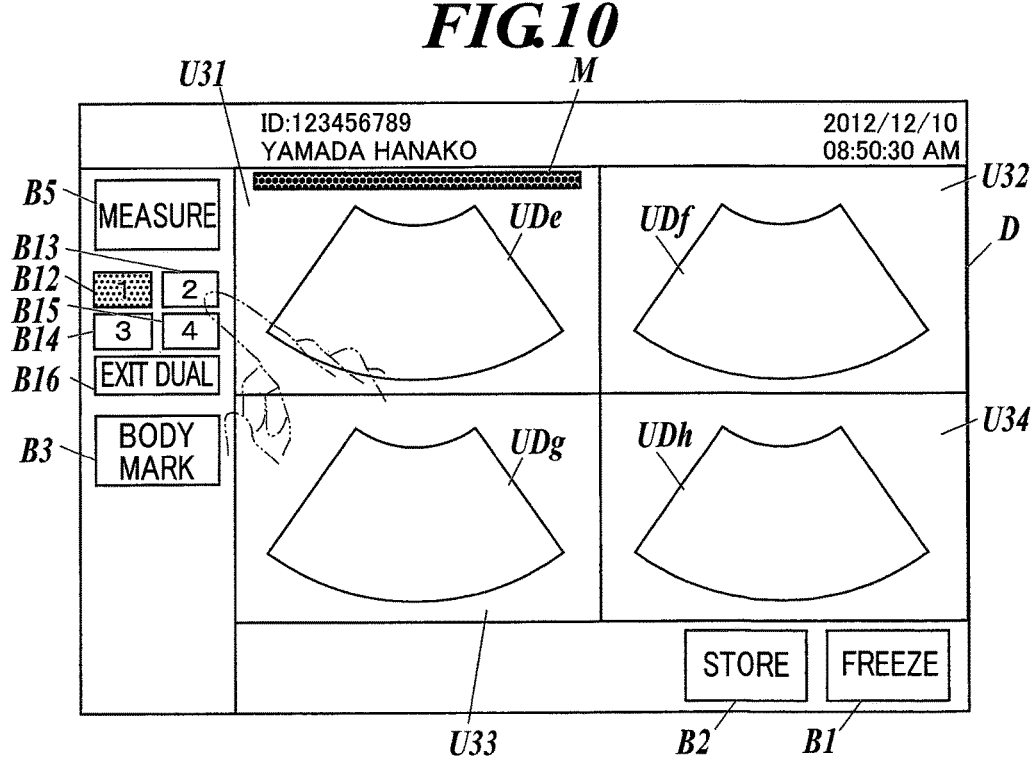
FIG. 10 is a diagram describing an example of an ultrasound image diagnostic screen.
Figure 11:
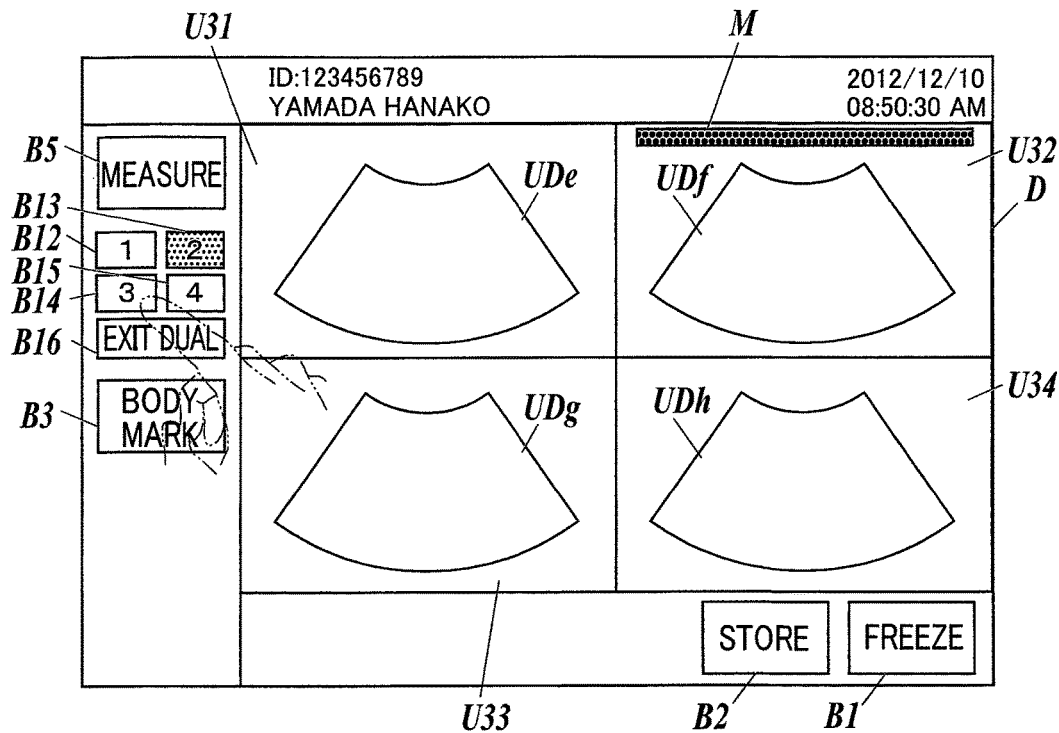
FIG. 11 is a diagram describing an example of an ultrasound image diagnostic screen.
Figure 12:
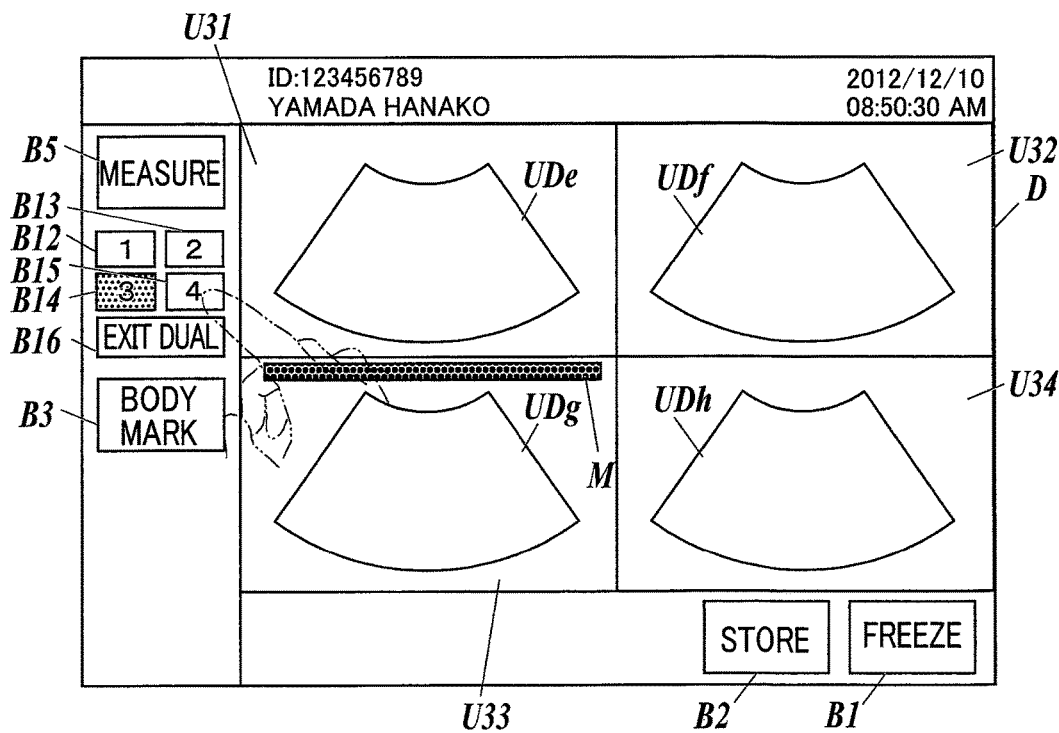
FIG. 12 is a diagram describing an example of an ultrasound image diagnostic screen.
Figure 13:
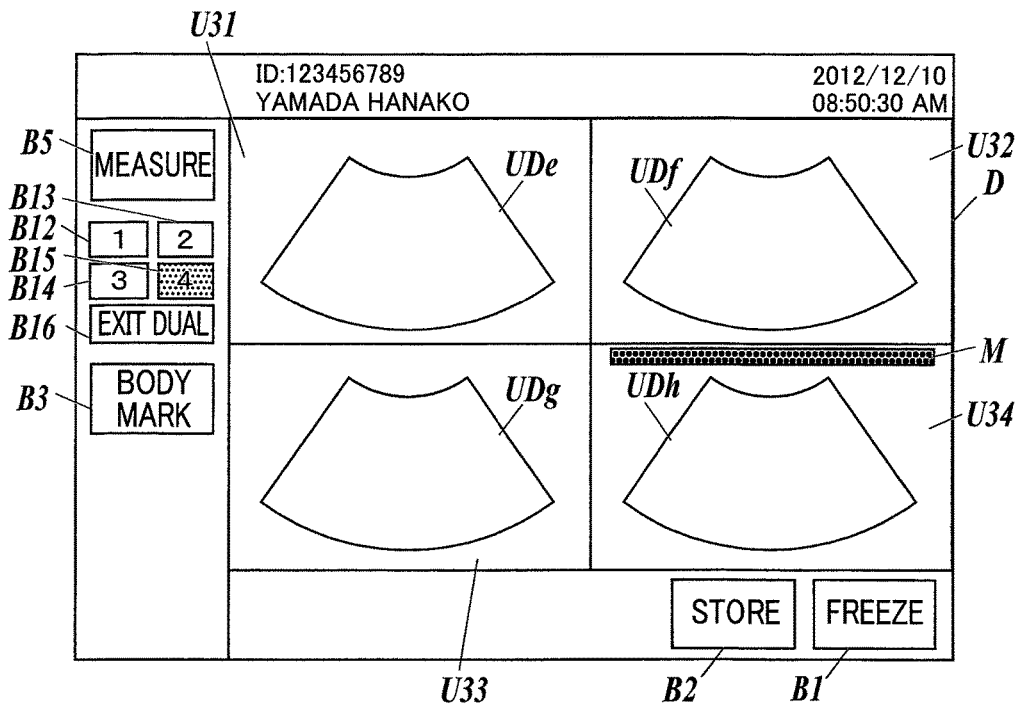
FIG. 13 is a diagram describing an example of an ultrasound image diagnostic screen.

Alternatively, in a case where the dual display mode is set as advancing to the quadruple screen display mode, when the operation of touching the dual display mode advancing button reception region is received, as shown in FIG. 10, the ultrasound image display region U1 is divided into four pieces, and the display format is changed so that the first display region U31, the second display region U32, the third display region U33, and the fourth display region U34 are provided aligned in a matrix shape. Ultrasound images UDe, UDf, UDg, and UDh are displayed respectively in the first display region U31, the second display region U32, the third display region U33, and the fourth display region U34. In the display region where the dual display mode advancing button B4 is displayed, instead of this button, a first button B12, a second button B13, a third button B14, and a fourth button B15 are displayed aligned in a matrix shape on the upper side and a dual display mode exit button B16 is displayed on the lower side of the display region. In the quadruple screen display mode, any one among the first display region U31, the second display region U32, the third display region U33, and the fourth display region U34 is active. An active mark M is displayed near the upper edge of the active display region of any one among the first display region U31, the second display region U32, the third display region U33, and the fourth display region U34. The first operation reception region is set in the position where the first button B12 is displayed, the second operation reception region is set in the position where the second button B13 is displayed, the third operation reception region is set in the position where the third button B14 is displayed, and the fourth operation reception region is set in the position where the fourth button B15 is displayed. When the operation of touching each operation reception region is received, the active display region is switched. In other words, when the first button B12 is touched, the first display region U31 becomes active, when the second button B13 is touched, the second display region U32 becomes active, when the third button B14 is touched, the third display region U33 becomes active, and when the fourth button B15 is touched, the fourth display region U34 becomes active. For example, as shown in FIG. 10, when the first display region U31 is active and the second button B13 is touched, as shown in FIG. 11, the second display region U32 becomes active. When the third button B14 is touched, as shown in FIG. 12, the third display region U33 becomes active. When the fourth button B15 is touched, as shown in FIG. 13, the fourth display region U34 becomes active. A single display mode advancing button reception region is set in the position where the dual display mode exit button B16 is displayed. When the single display mode advancing button reception region is touched, the display format advances to the single display mode as described above.

According to the present embodiment, the above-described measuring processing can be performed as described below.

Figure 14:
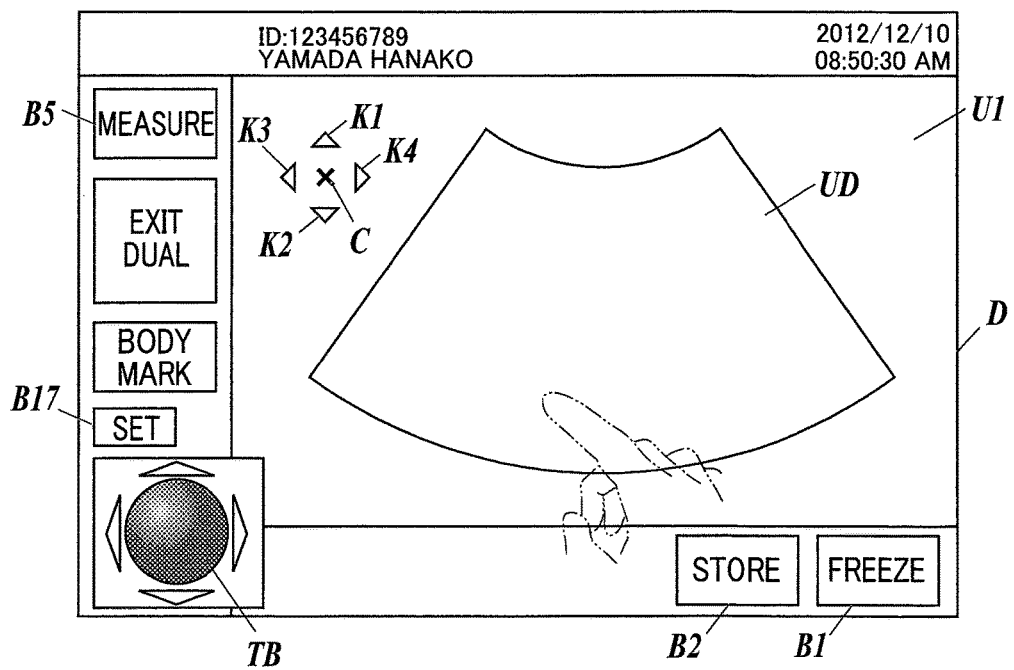
FIG. 14 is a diagram describing an example of an ultrasound image diagnostic screen.
Figure 15:
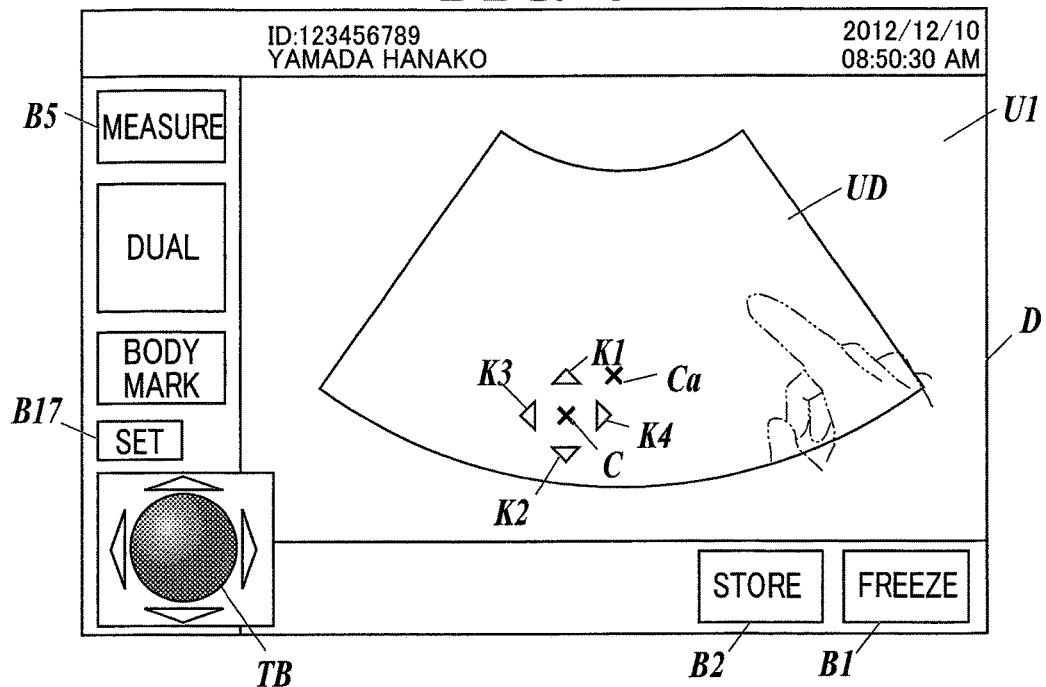
FIG. 15 is a diagram describing an example of an ultrasound image diagnostic screen.
Figure 16:
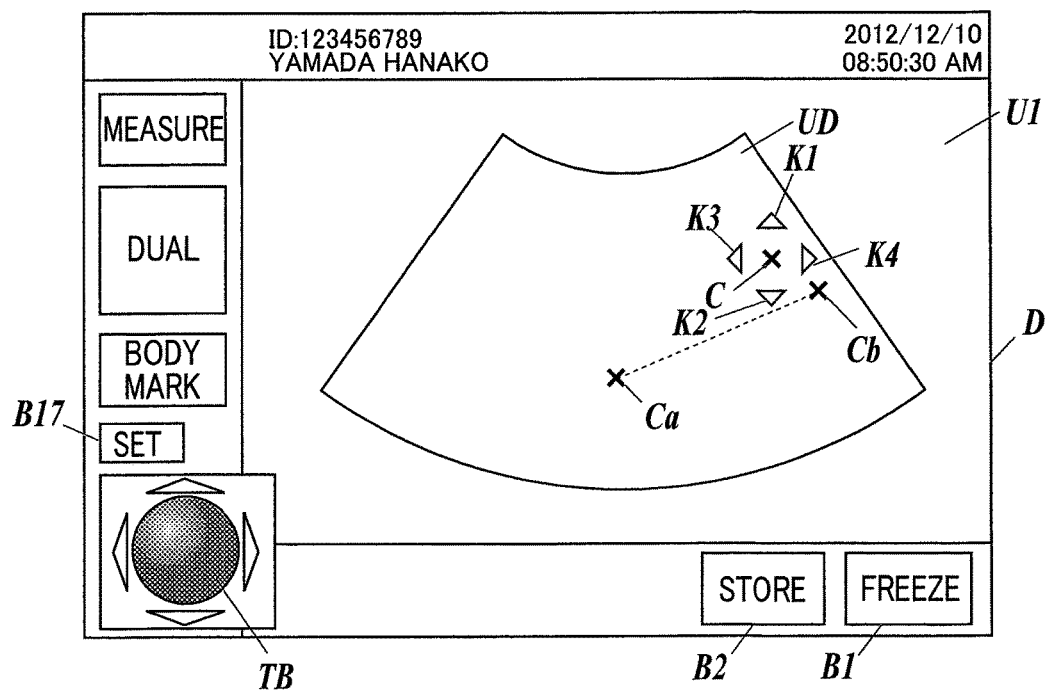
FIG. 16 is a diagram describing an example of an, ultrasound image diagnostic screen.

First, when the measure button B5 is touched on the ultrasound diagnostic screen D, as shown in FIG. 14, the cursor C is displayed on the ultrasound image display region U1 and the trackball image TB and the set button B17 are displayed in the lower left side of the ultrasound diagnostic screen D so as to be able to perform measurement. When the measurement is performed, it is necessary to input two points which are the start point and the end point. When the start point is input, for example, as shown in FIG. 14, when any position is touched, the display of the cursor C moves to the touched position. Here, near the above, below, left, and right areas of the cursor C, cursor keys K1 to K4 are displayed, and the cursor keys K1 to K4 are touched to finely adjust the position of the cursor C. Then, when the set button B17 is touched, as shown in FIG. 15, the start point Ca is set. Next, when the end point is input, as shown in FIG. 15, when any position other than the start point Ca is touched, the display of the cursor C moves to the touched position. Then, when the set button B17 is touched, as shown in FIG. 16, the end point Cb is set. Then, a direct line connecting the two points of the start point Ca and the end point Cb is displayed with a broken line, and the distance between the two points is displayed as a measured value near the line. When the end point Cb is set, the cursor C is displayed near the end point Cb, another start point and end point can be set, and further measurement of another set of two points can be performed. As described above, according to the present embodiment, the display position of the cursor C can be set by operation of touching, and it is possible to set the display position of the cursor C by less movement of the hand. Moreover, the display position of the cursor C can be finely adjusted by operating the cursor keys K1 to K4. Therefore, it is possible to set the display position of the cursor C more accurately, and it is possible to reduce mistake of setting due to the hand or finger covering the display of the cursor C.

Figure 17:
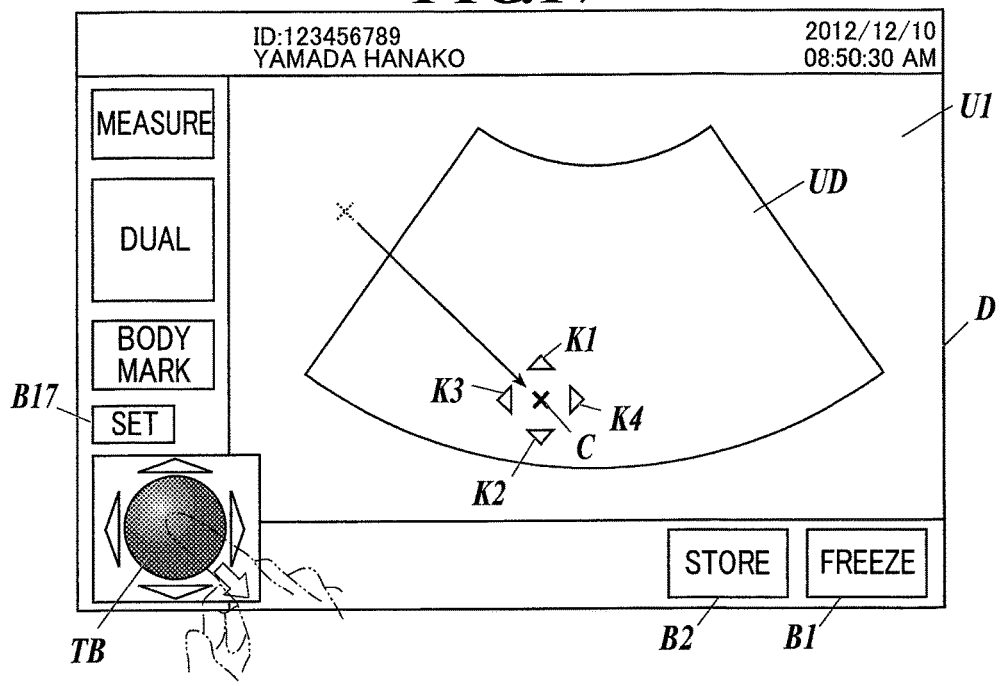
FIG. 17 is a diagram describing an example of an ultrasound image diagnostic screen.
Figure 18:
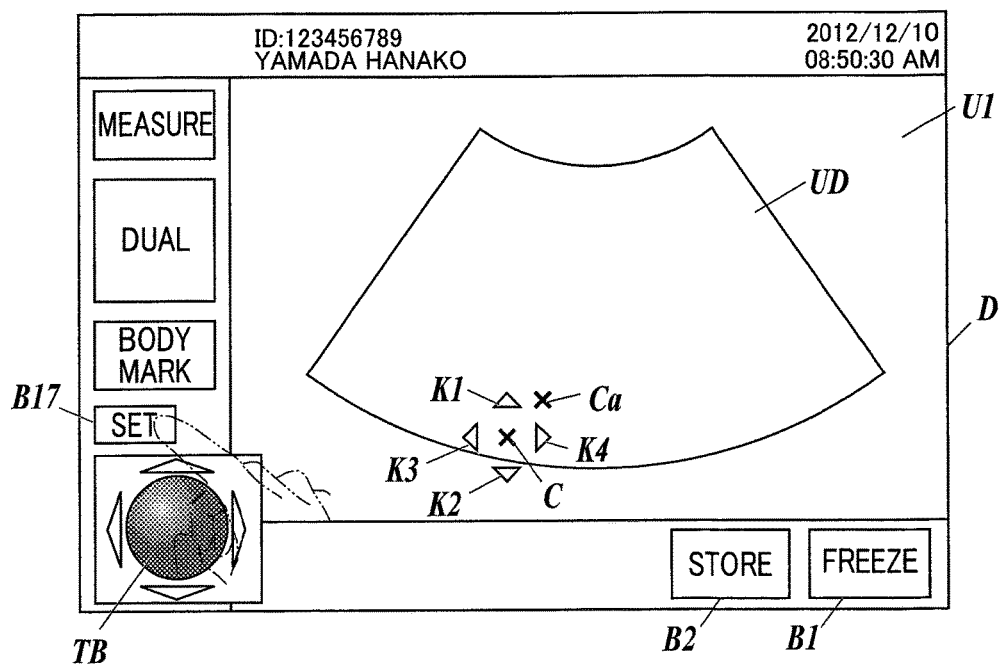
FIG. 18 is a diagram describing an example of an ultrasound image diagnostic screen.

According to the present embodiment, it is possible to move the display position of the cursor C by operation of touching the trackball image TB. Specifically, as shown in FIG. 17, by sliding the finger in any direction while touching the trackball image TB, it is possible to move the display position of the cursor C in the direction that the finger is slid to. Then, as shown in FIG. 18, after the position of the cursor C is moved to any position by touching the trackball image TB, the start point Ca can be set by touching the set button B17. The end point Cb can be similarly set. As described above, according to the present embodiment, the display position of the cursor C can be set by operation of touching the trackball image TB. Therefore, it is possible to set the display position of the cursor C indirectly in a position away from the display region of the ultrasound image. Therefore, it is possible to set the display position of the cursor C without touching the display region of the ultrasound image, and it is possible to prevent the display region of the ultrasound image on the display unit 107a from becoming dirty due to touching and the ultrasound image becoming difficult to see. Moreover, it is possible to reduce mistake of setting due to the hand or finger covering the display of the cursor C.

Figure 19:
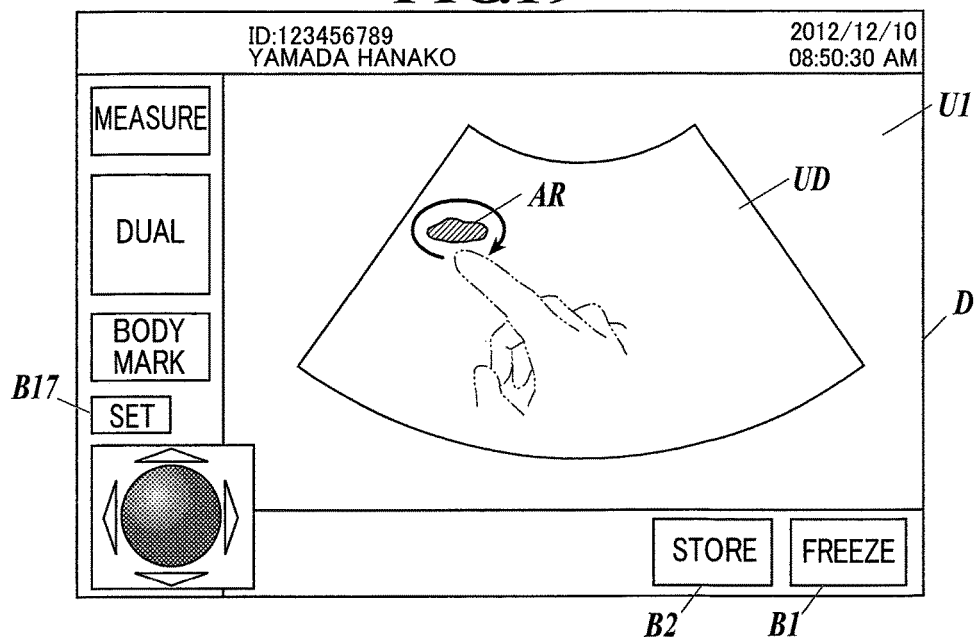
FIG. 19 is a diagram describing an example of an ultrasound image diagnostic screen.
Figure 20:
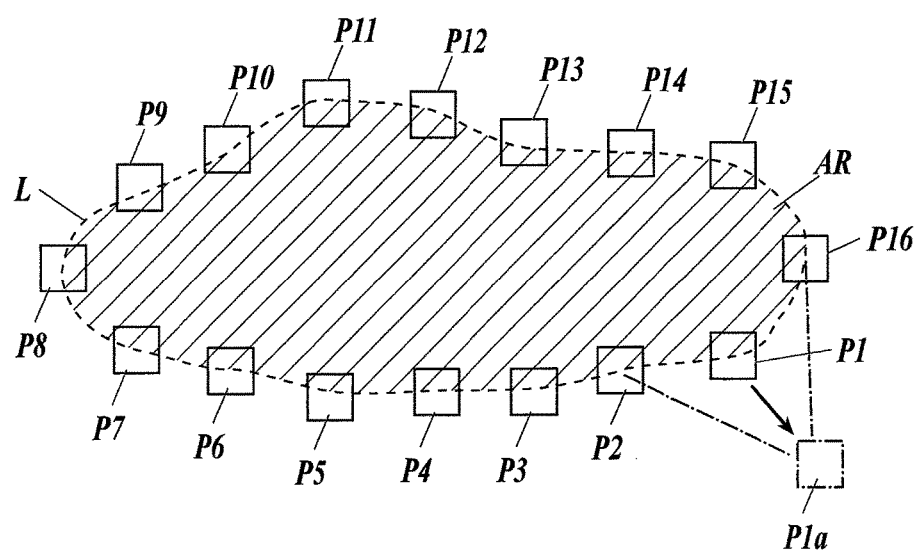
FIG. 20 is a diagram describing an area tracing function.

The ultrasound diagnostic imaging apparatus 1 of the present embodiment includes an area tracing function. The area tracing function is a function which marks a specific site on the ultrasound image. As shown in FIG. 19, for example, a site AR is shown as the specific site on the ultrasound image UD. The site AR is shown with luminance different from the surrounding sites. When the site AR is marked by the area tracing function, first, an area near the site AR is touched and the finger touching the area is slid so as to surround the site AR. Then, the portion with a large difference of luminance in the surrounded region is extracted as an edge. When it is detected that a closed curve is formed by the edge, as shown in FIG. 20, a boundary line L in a shape matching the closed curve is drawn. Then, in the present embodiment, a plurality (for example, 16) of adjusting points P1 to P16 are displayed along the boundary line L, and by touching and sliding the adjusting points P1 to P16 to change the display position of the adjusting points P1 to P16, the shape of the boundary line L can be changed. For example, when the adjusting point P1 is touched and slid, and the display position of the adjusting point P1 is changed to an adjusting point P1a, the shape is changed so that the boundary line L passes through the adjusting point P1a. The number of adjusting points can be set freely, and as the number of adjusting points increase, the shape of the boundary line L can be set in detail, whereas as the number of adjusting points decrease, the setting of the shape of the boundary line L can be set more easily. As described above, according to the present embodiment, according to the above described configuration, it is possible to mark a specific site by reducing the steps of operation even if the shape of the specific site is complicated, and it is possible to reduce the burden of operation on the operator. Moreover, by changing the display position of the adjusting points P1 to P16, it is possible to change the shape of the boundary line L. Therefore, it is possible to accurately mark the specific site and the convenience is enhanced.

Figure 21:
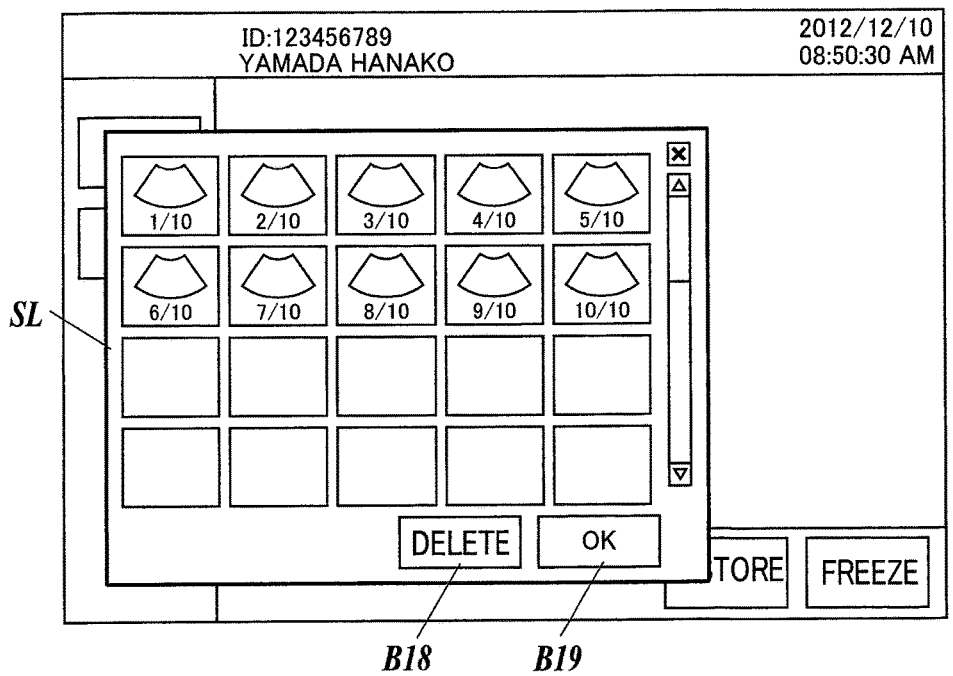
FIG. 21 is a diagram describing an example of an ultrasound image diagnostic screen.
Figure 22:
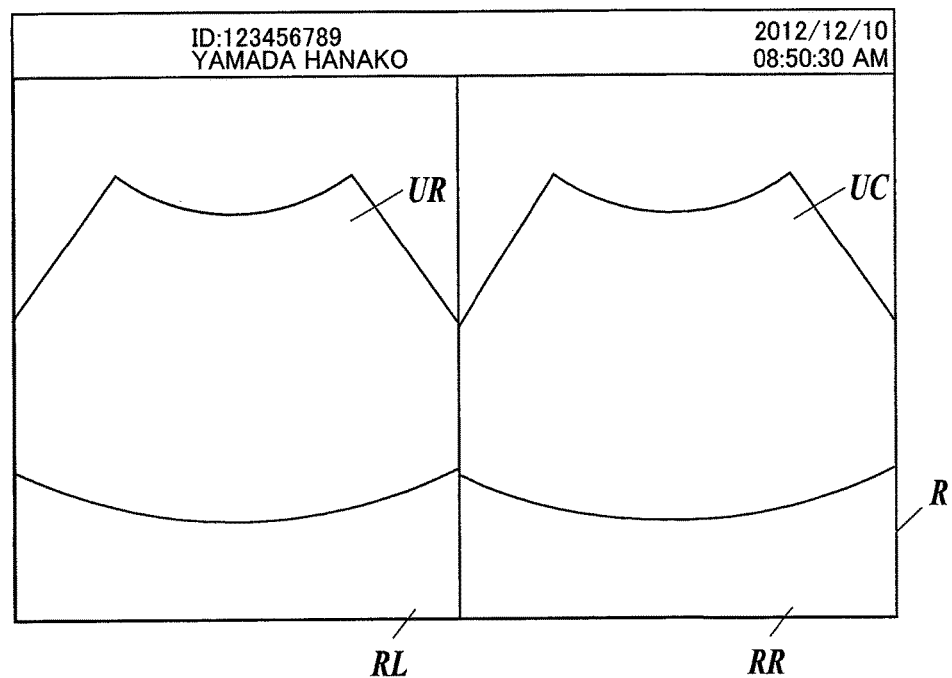
FIG. 22 is a diagram describing an example of a review screen.

According to the present embodiment, when operation to advance to the review screen is performed when the scanning operation ends and the examination ends as described above, the screen advances to the obtained image editing mode. For example, as shown in FIG. 21, in the obtained image editing mode, a thumbnail list SL is displayed, and thumbnail images based on the stored ultrasound image data of the patient who is examined are displayed. With this, for example, it is possible to confirm whether there is a site of examination which is not obtained yet. Here, when there is an ultrasound image displayed on the thumbnail list SL which is not necessary, the image can be deleted by touching the thumbnail image desired to be deleted and then touching the delete button B18. When the OK button B19 is touched after any of the thumbnail images displayed in the thumbnail list SL is touched, the review screen R as shown in FIG. 22 is displayed on the display screen of the display unit 107a. A left side ultrasound image display region RL and a right side ultrasound image display region RR are positioned in the review screen R. An ultrasound image UR corresponding to the thumbnail selected from the thumbnail list SL is displayed in the left side ultrasound image display region RL, and for example, an ultrasound image UC obtained when the scanning operation ends is displayed in the right side ultrasound image display region RR. As described above, in the present embodiment, the thumbnail of the ultrasound image obtained by performing the examination is displayed as a list on the thumbnail list SL. Therefore, it is possible to confirm whether there is an ultrasound image which is not obtained yet or whether an unnecessary ultrasound image is obtained. With this, it is possible to respond to the above by deleting unnecessary ultrasound image data, or by performing examination again when there is an ultrasound image which needs to be obtained, and it is possible to enhance efficiency of examination.

Second Embodiment

Next, the second embodiment is described. In the second embodiment, when the display format advances to the dual screen display mode, the active display region is switched by directly touching the display region. With such configuration, according to the second embodiment, it is possible to switch the active display region more intuitively.

The specific configuration of the ultrasound diagnostic imaging apparatus 1 of the second embodiment is similar to the ultrasound diagnostic imaging apparatus 1 of the first embodiment. Therefore, the same reference numerals are applied and the description is omitted.

For example, in the second embodiment, when the scanning operation starts as described in the first embodiment, if the dual display mode advancing button B4 is touched, the display format advances from the single display mode to the dual screen display mode or the quadruple screen display mode.

Figure 23:
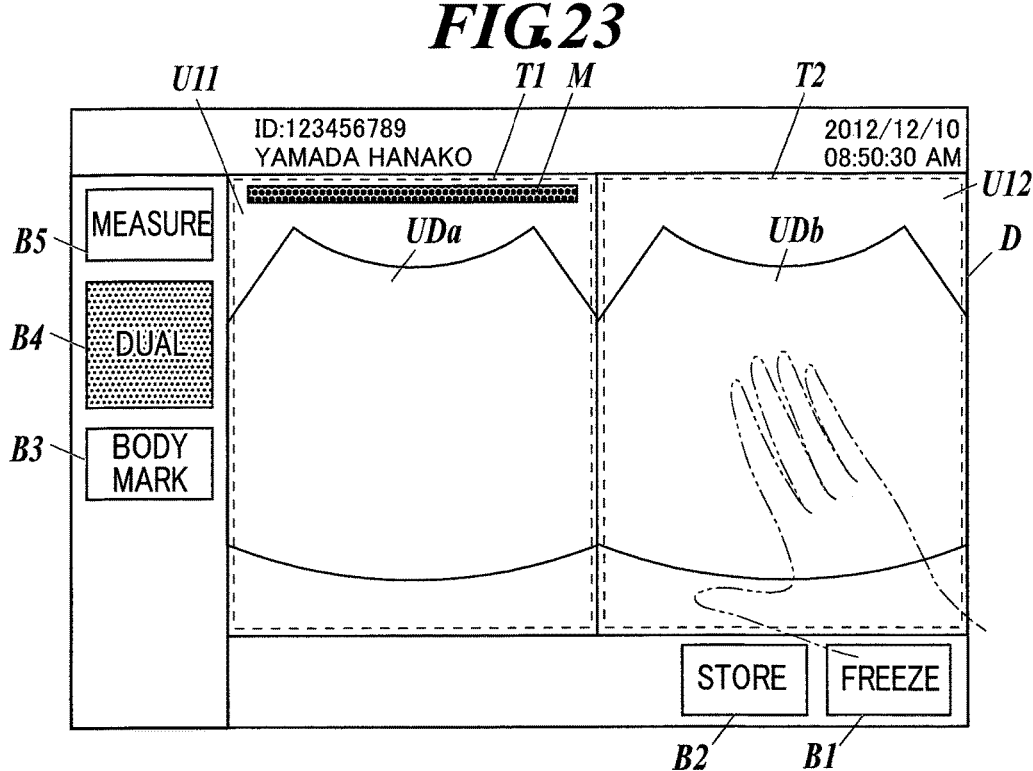
FIG. 23 is a diagram describing an example of an ultrasound image diagnostic screen.
Figure 24:
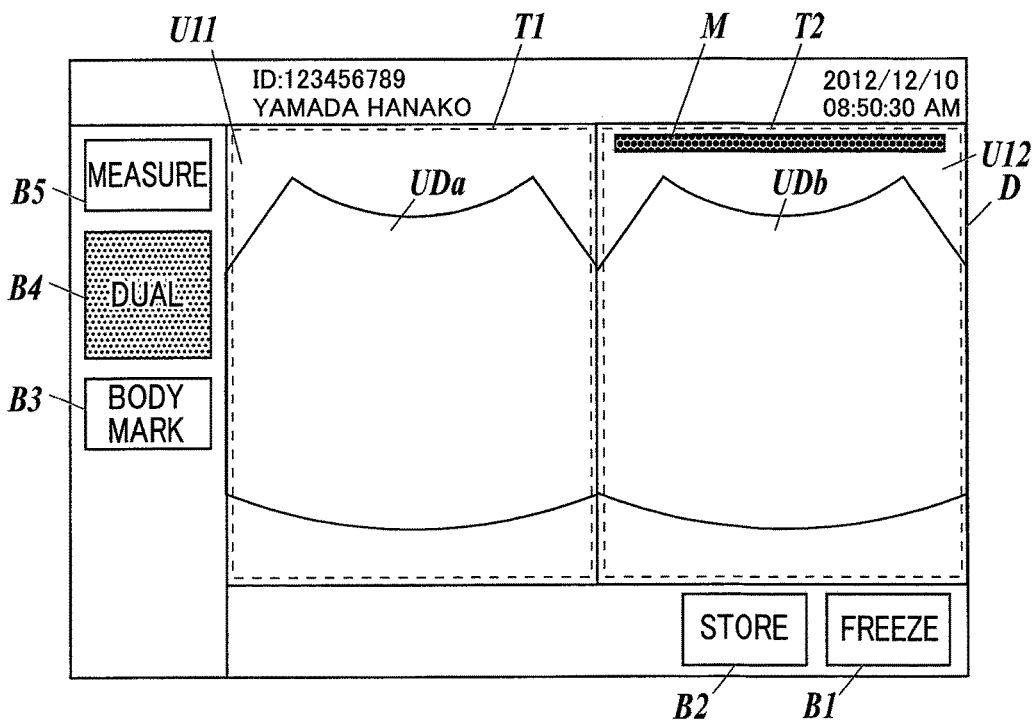
FIG. 24 is a diagram describing an example of an ultrasound image diagnostic screen.

For example, in a case where the single display mode advances to the horizontal display mode, the ultrasound diagnostic screen D as shown in FIG. 23 is displayed on the display screen of the display unit 107a. In the ultrasound diagnostic screen D, the left side display region U11 and the right side display region U12 are provided. Ultrasound images UDa and UDb are displayed respectively in the left side display region U11 and the right side display region U12. A left side operation reception region T1 is set in a position corresponding to the left side display region U11, and a right side operation reception region T2 is set in a position corresponding to the right side display region U12. When operation of touching is received in each operation reception region, the active display region is switched. Similar to the first embodiment, an active mark M is displayed near the upper edge of the active display region. For example, as shown in FIG. 23, when the right side operation reception region T2 is touched when the left side display region U11 is active, as shown in FIG. 24, the right side display region U12 becomes active. It is possible to advance from the dual screen display mode to the single display mode by touching the dual display mode advancing button B4 again.

Figure 25:
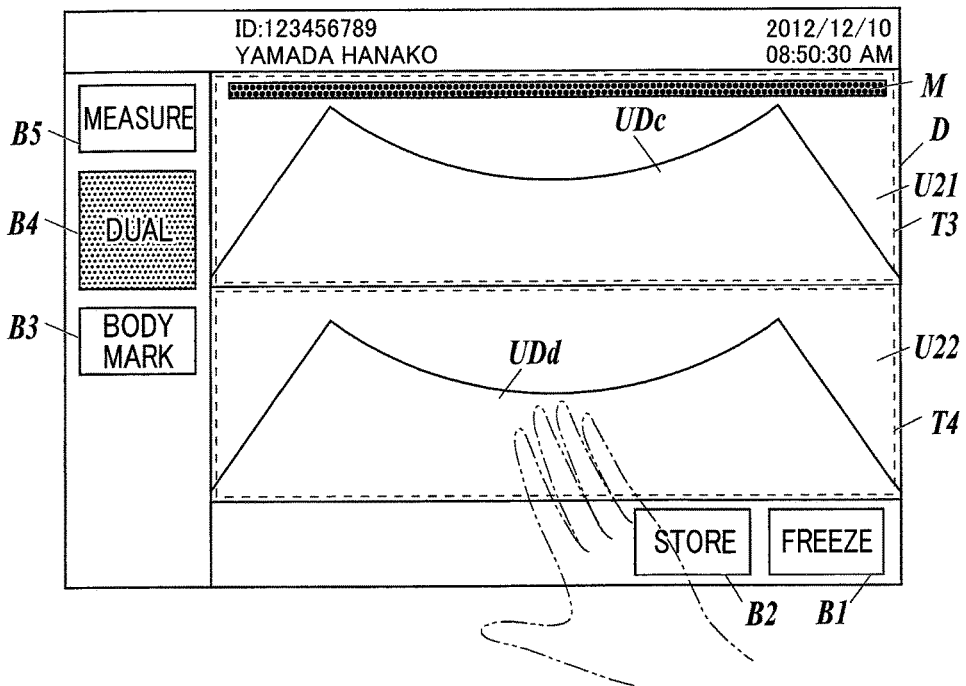
FIG. 25 is a diagram describing an example of an ultrasound image diagnostic screen.
Figure 26:
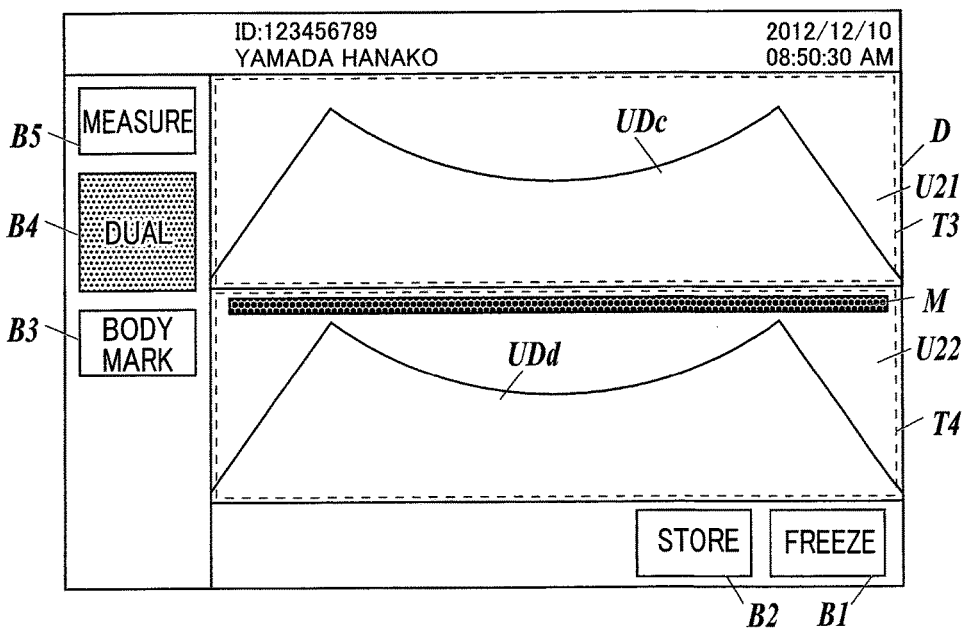
FIG. 26 is a diagram describing an example of an ultrasound image diagnostic screen.

Alternatively, in a case where the single display mode advances to the vertical display mode, the ultrasound diagnostic screen D as shown in FIG. 25 is displayed on the display screen of the display unit 107a. In the ultrasound diagnostic screen D, the upper side display region U21 and the lower side display region U22 are provided. Ultrasound images UDc and UDd are displayed respectively in the upper side display region U21 and the lower side display region U22. An upper side operation reception region T3 is set in a position corresponding to the upper side display region U21, and a lower side operation reception region T4 is set in a position corresponding to the lower side display region U22. When operation of touching is received in each operation reception region, the active display region is switched. For example, as shown in FIG. 25, when the lower side operation reception region T4 is touched when the upper side display region U21 is active, as shown in FIG. 26, the lower side display region U22 becomes active.

As described above, according to the first and second embodiment, the touch panel 107b is provided overlapped with the display screen of the display unit 107a. The control unit 108 is able to execute the vertical display mode which displays two ultrasound images aligned vertically on the display screen of the display unit 107a, and the horizontal display mode which displays two ultrasound images aligned horizontally on the display screen of the display unit 107a. In the vertical display mode, the control unit 108 sets the upper side operation reception region and the lower side operation reception region of the touch panel 107b aligned vertically. When the control unit 108 detects operation of touching the upper side operation reception region, the control unit 108 sets the ultrasound image displayed on the upper side to the selected state, and when the control unit 108 detects operation of touching the lower side operation reception region, the control unit 108 sets the ultrasound image displayed on the lower side to the selected state. In the horizontal display mode, the control unit 108 sets the left side operation reception region and the right side operation reception region of the touch panel 107b aligned horizontally. When the control unit 108 detects operation of touching the left side operation reception region, the control unit 108 sets the ultrasound image displayed on the left side to the selected state, and when the control unit 108 detects operation of touching the right side operation reception region, the control unit 108 sets the ultrasound image displayed on the right side to the selected state. As a result, in the vertical display mode and the horizontal display mode, a physical interface such as keys to switch the display region in the selected state is not necessary, and it is possible to store space. Moreover, it is possible to intuitively operate switching of the display region in the selected state.

According to the first embodiment, the control unit 108 is able to execute the single display mode to display one ultrasound image on the display screen of the display unit 107a. In the single display mode, the control unit 108 displays the dual display mode advancing button B4 in a predetermined region on the display screen of the display unit 107a and sets a dual display mode advancing button reception region of the touch panel 107b corresponding to the display of the dual display mode advancing button B4. When the control unit 108 detects the operation of touching the dual display mode advancing button reception region, the control unit 108 advances from the single display mode to the vertical display mode or the horizontal display mode. When the control unit 108 advances the display mode to the vertical display mode, the control unit 108 sets the upper side operation reception region and the lower side operation reception region in the region where the dual display mode advancing button reception region is set in the single display mode. When the control unit 108 advances the display mode to the horizontal display mode, the control unit 108 sets the left side operation reception region and the right side operation reception region in the region where the dual display mode advancing button reception region is set in the single display mode. As a result, it is possible to collectively position the operation unit for advancing and switching from the single display mode to the dual display mode, and the operation unit for switching the ultrasound image in the selected state. Therefore, the operability is enhanced.

According to the first embodiment, in the vertical display mode and the horizontal display mode, the control unit 108 further sets the single display mode advancing button reception region in the region where the dual display mode advancing button reception region is set in the single display mode. In the vertical display mode or the horizontal display mode, when the control unit 108 detects the operation of touching the single display mode advancing button reception region, the control unit 108 advances the display mode from the vertical display mode or the horizontal display mode to the single display mode. As a result, it is possible to further collect the units for advancing and switching from the vertical display mode and the horizontal display mode to the single display mode. Therefore, the operability is enhanced.

According to the second embodiment, in the vertical display mode, the control unit 108 sets the upper side operation reception region and the lower side operation reception region corresponding to each of the display of the two ultrasound images displayed aligned vertically. In the horizontal display mode, the control unit 108 sets the left side operation reception region and the right side operation reception region corresponding to each of the display of the two ultrasound images displayed aligned horizontally. As a result, it is possible to more intuitively perform operation of switching the display region in the selected state. Therefore, the operability is enhanced.

According to the first and the second embodiments, the control unit 108 is able to execute the quadruple screen display mode to display four ultrasound images aligned in a matrix shape on the display screen of the display unit 107a. In the quadruple screen display mode, the control unit 108 sets the first operation reception region, the second operation reception region, the third operation reception region, and the fourth operation reception region of the touch panel 107b aligned in a matrix shape. When the control unit 108 detects operation of touching the first operation reception region, the control unit 108 sets the first ultrasound image among the four ultrasound images to the selected state, when the control unit 108 detects operation of touching the second operation reception region, the control unit 108 sets the second ultrasound image among the four ultrasound images to the selected state, when the control unit 108 detects operation of touching the third operation reception region, the control unit 108 sets the third ultrasound image among the four ultrasound images to the selected state, and when the control unit 108 detects operation of touching the fourth operation reception region, the control unit 108 sets the fourth ultrasound image among the four ultrasound images to the selected state. As a result, in the quadruple screen display mode, a physical interface such as keys to switch the display region in the selected state is not necessary, and it is possible to store space. Moreover, in the quadruple screen display mode, it is possible to intuitively operate switching of the display region in the selected state.

The description of the embodiment of the present invention is one example of the ultrasound diagnostic imaging apparatus of the present invention, and the present invention is not limited to the above. The detailed configuration and operation of the functional units composing the ultrasound diagnostic imaging apparatus can be suitably changed.

According to the present embodiment, in the dual screen display mode and the quadruple screen display mode, the dual display mode exit button is provided in the region where the dual display mode advancing button is displayed, however, the dual display mode exit button does not have to be provided.

The present embodiment does not have to execute the quadruple screen display mode.

The present embodiment does not have to perform the measuring processing. Moreover, the present embodiment does not have to be provided with the area tracing function.

Figure 27:
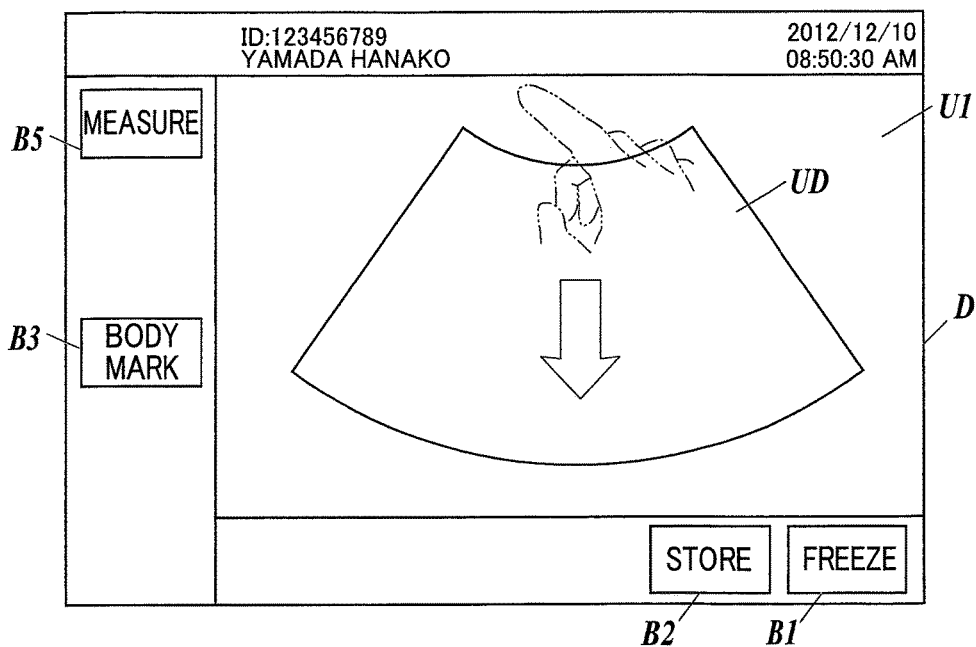
FIG. 27 is a diagram describing an example of an ultrasound image diagnostic screen.
Figure 28:
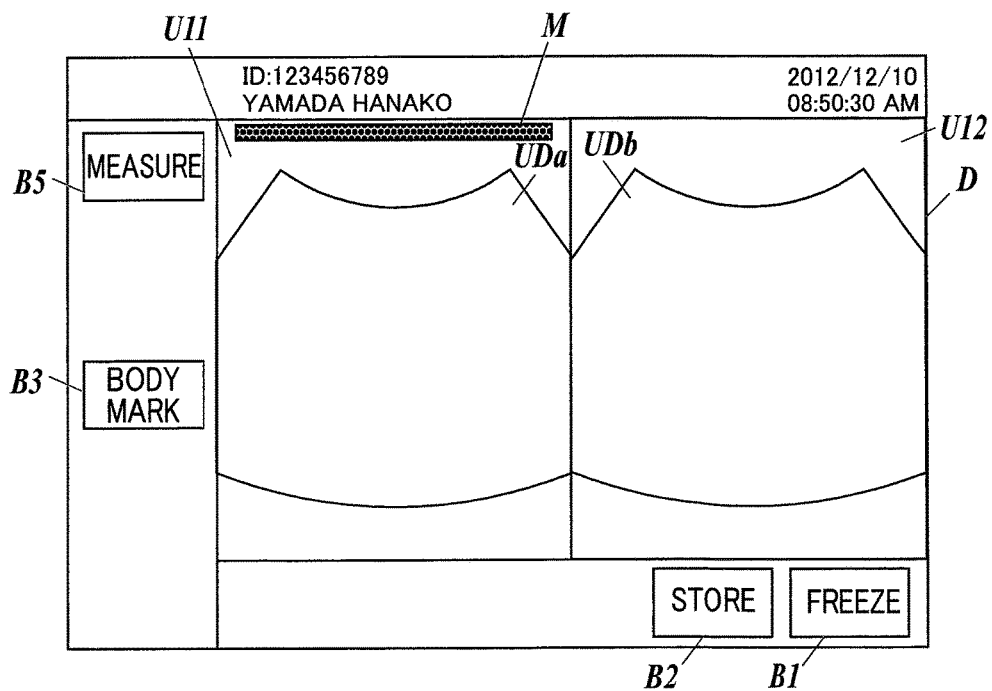
FIG. 28 is a diagram describing an example of an ultrasound image diagnostic screen.

In the present embodiment, the display mode is advanced to the dual screen display mode or the quadruple screen display mode by operation of touching the dual display mode advancing button or operation of a predetermined key provided on the operation input unit 101. However, for example, it is possible to set the apparatus so that in the single display mode, as shown in FIG. 27, when an approximate area of the central upper edge section of the display region of the display unit 107a is touched and the finger is slid in the vertical direction while touching the area, as shown in FIG. 28, the display mode advances to the horizontal display mode.

Figure 29:
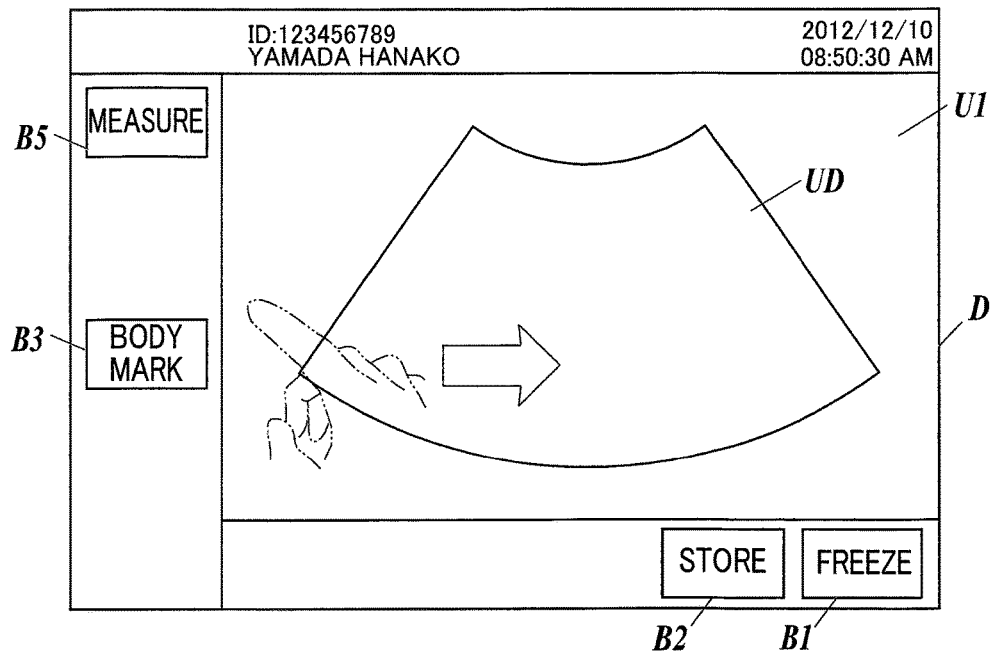
FIG. 29 is a diagram describing an example of an ultrasound image diagnostic screen.
Figure 30:
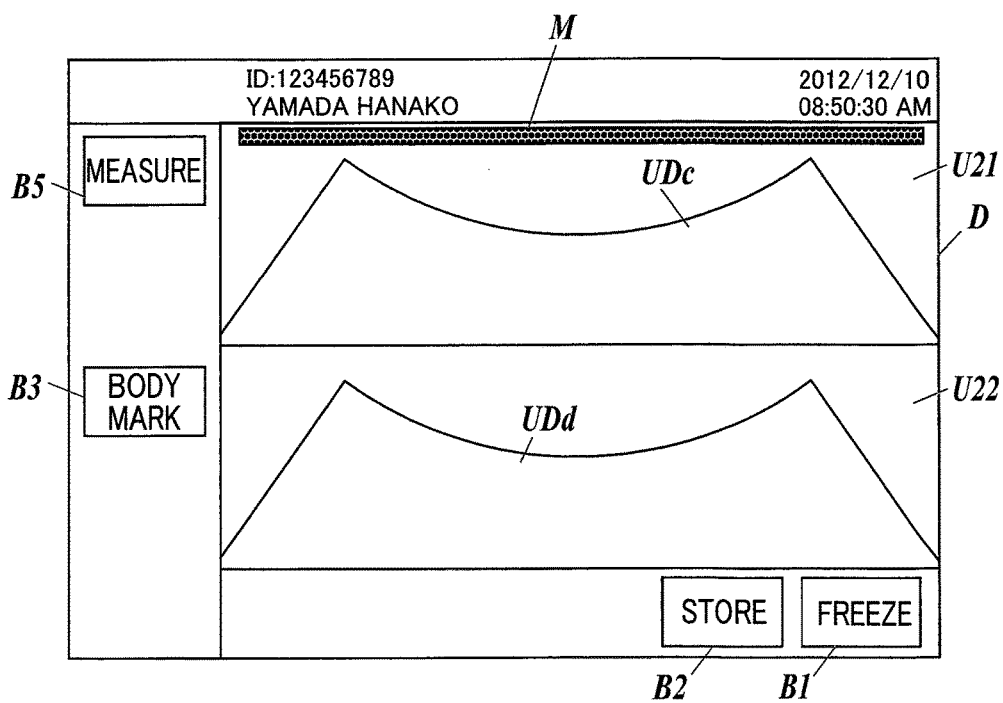
FIG. 30 is a diagram describing an example of an ultrasound image diagnostic screen.

Alternatively, for example, it is possible to set the apparatus so that in the single display mode, as shown in FIG. 29, when an approximate area of the central left edge section of the display region of the display unit 107a is touched, and the finger is slid in the horizontal direction while touching the area, as shown in FIG. 30, the display mode advances to the vertical display mode. Here, it is also possible to set the apparatus so that when an approximate area of the central upper edge section is touched and the finger is slid in the vertical direction while touching the area, the display mode advances to the quadruple screen display mode.

Figure 31:
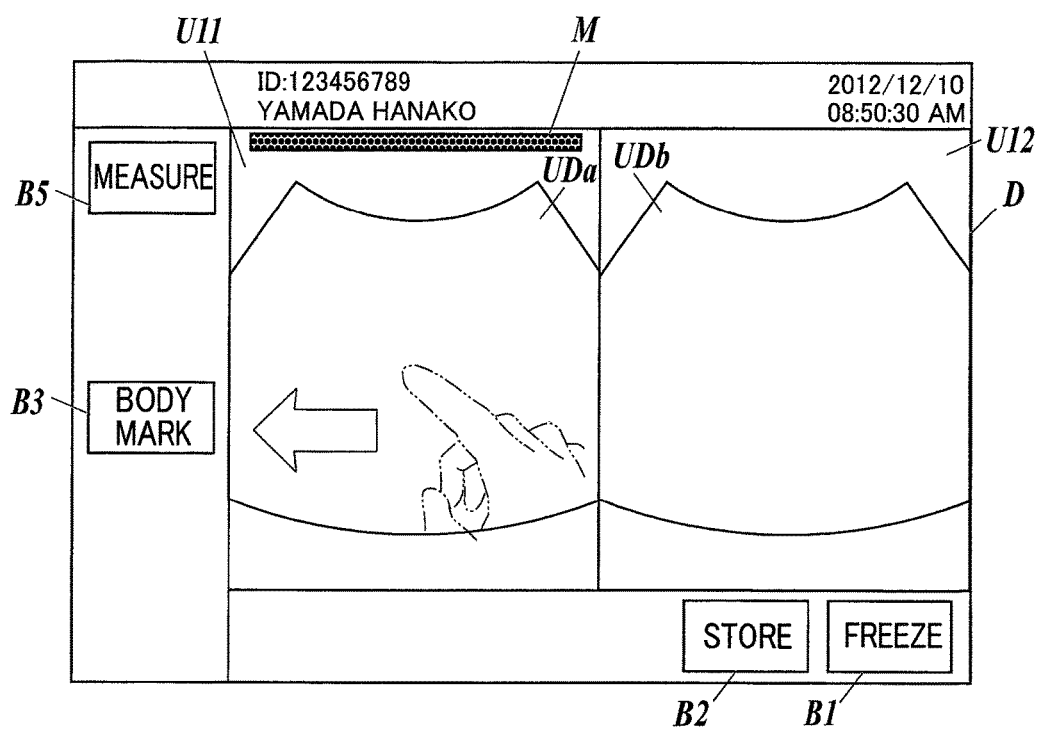
FIG. 31 is a diagram describing an example of an ultrasound image diagnostic screen.

According to the present embodiment, the display mode advances from the dual screen display mode and the quadruple screen display mode to the single display mode by operation of touching the dual display mode exit button or operation of the predetermined key provided on the operation input unit 101. However, for example, it is possible to set the apparatus so that as shown in FIG. 31, the display mode advances to the single display mode by touching an approximate center of the active display region (in FIG. 31, left side display region U11), and sliding the finger toward the side edge section of the display region of the display unit 107a while touching.

According to the present embodiment, a hard disk or a non-volatile semiconductor memory is used as a computer readable medium including the program of the present invention, however, the present invention is not limited to the above. As other computer readable mediums, a portable recording medium such as a CD-ROM, etc. can be applied. As the medium providing the data of the program regarding the present invention through communication lines, carrier waves can also be applied.

The present application is based on Japanese Patent Application No. 2013-018012 filed on Feb. 1, 2013 to the Japanese Patent Office, which shall be a basis for correcting mistranslations.

What is claimed is:

1. An ultrasound diagnostic imaging apparatus which outputs a transmitting ultrasound to a test subject, obtains a receiving signal by receiving a reflecting ultrasound from the test subject, generates ultrasound image data based on the obtained receiving signal, and displays an ultrasound image on a display screen of a display based on the ultrasound image data, the ultrasound diagnostic imaging apparatus comprising:
   a touch panel provided overlapped on the display screen of the display; and
   a processor which executes a vertical display mode to display two vertical ultrasound display regions in which two ultrasound images are respectively aligned vertically on the display screen of the display and a horizontal display mode to display two horizontal ultrasound display regions in which two ultrasound images are respectively aligned horizontally on the display screen of the display,
   wherein in the vertical display mode, the processor sets an upper side operation reception region and a lower side operation reception region aligned vertically on the touch panel, and when the processor detects an operation of touching the upper side operation reception region, the processor sets an ultrasound image displayed on an upper side to a selected state and displays an ultrasound display region containing the ultrasound image displayed on the upper side to contain a mark to indicate that the ultrasound display region containing the ultrasound image displayed on the upper side contains an ultrasound image in the selected state, and when the processor detects an operation of touching the lower side operation reception region, the processor sets an ultrasound image displayed on a lower side to the selected state and displays an ultrasound display region containing the ultrasound image displayed on the lower side to contain the mark to indicate that the ultrasound display region containing the ultrasound image displayed on the lower side contains an ultrasound image in the selected state;
   wherein in the horizontal display mode, the processor sets a left side operation reception region and a right side operation reception region aligned horizontally on the touch panel, and when the processor detects an operation of touching the left side operation reception region, the processor sets an ultrasound image displayed on a left side to the selected state and displays an ultrasound display region containing the ultrasound image displayed on the left side to contain the mark to indicate that the ultrasound display region containing the ultrasound image displayed on the left side contains an ultrasound image in the selected state, and when the processor detects an operation of touching the right side operation reception region, the processor sets an ultrasound image displayed on a right side to the selected state and displays an ultrasound display region containing the ultrasound image displayed on the right side to contain the mark to indicate that the ultrasound display region containing the ultrasound image displayed on the right side contains an ultrasound image in the selected state;
   wherein in the vertical display mode the upper side operation reception region and the lower side operation reception region are displayed in a region of the touch panel so as not to overlap with the two vertical ultrasound display regions, and in the horizontal display mode the left side operation reception region and the right side operation reception region are displayed in a region of the touch panel so as not to overlap with the two horizontal ultrasound display regions.

2. The ultrasound diagnostic imaging apparatus of claim 1, wherein:
   the processor executes a single display mode to display one ultrasound image on the display screen of the display;
   in the single display mode, the processor displays a dual screen display mode advancing button in a predetermined region on the display screen of the display;
   the processor sets a dual screen display mode advancing button reception region on the touch panel corresponding to the display of the dual screen display mode advancing button;
   when the processor detects an operation of touching the dual screen display mode advancing button reception region, the processor advances a display mode from the single display mode to the vertical display mode or the horizontal display mode;

when the processor advances the display mode to the vertical display mode, the processor sets the upper side operation reception region and the lower side operation reception region in a region where the dual screen display mode advancing button reception region is set in the single display mode; and when the processor advances the display mode to the horizontal display mode, the processor sets the left side operation reception region and the right side operation reception region in a region where the dual screen display mode advancing button reception region is set in the single display mode.

3. The ultrasound diagnostic imaging apparatus of claim 2, wherein:

in the vertical display mode and the horizontal display mode, the processor further sets a single display mode advancing button reception region in a region where the dual screen display mode advancing button reception region is set in the single display mode; and in the vertical display mode and the horizontal display mode, when the processor detects an operation of touching the single display mode advancing button reception region, the processor advances the display mode from the vertical display mode or the horizontal display mode to the single display mode.

4. The ultrasound diagnostic imaging apparatus of claim 1, wherein:

the processor executes a quadruple screen display mode to display four ultrasound images aligned in a matrix shape on the display screen of the display;

in the quadruple screen display mode, the processor sets a first operation reception region, a second operation reception region, a third operation reception region, and a fourth operation reception region on the touch panel, the operation reception regions being aligned in a matrix shape;

when the processor detects an operation of touching the first operation reception region, the processor sets a first ultrasound image among the four ultrasound images to the selected state;

when the processor detects an operation of touching the second operation reception region, the processor sets a second ultrasound image among the four ultrasound images to the selected state;

when the processor detects an operation of touching the third operation reception region, the processor sets a third ultrasound image among the four ultrasound images to the selected state; and when the processor detects an operation of touching the fourth operation reception region, the processor sets a fourth ultrasound image among the four ultrasound images to the selected state.

5. The ultrasound diagnostic imaging apparatus of claim 1, wherein, the processor displays an ultrasound image in the selected state as a moving image, and the processor displays an ultrasound image in a non-selected state as a static image.

6. The ultrasound diagnostic imaging apparatus of claim 1, wherein the processor executes a single display mode to display one ultrasound image on the display screen of the display, and when an operation of sliding in a vertical direction is detected in the single display mode, the processor advances a display mode to the horizontal display mode.

7. The ultrasound diagnostic imaging apparatus of claim 1, wherein the processor executes a single display mode to display one ultrasound image on the display screen of the display, and when an operation of sliding in a horizontal direction is detected in the single display mode, the processor advances a display mode to the vertical display mode.

8. The ultrasound diagnostic imaging apparatus of claim 1, wherein when an operation of sliding in a vertical direction is detected in the vertical display mode, the processor advances a display mode to a quadruple screen display mode to display four ultrasound images aligned in a matrix shape on the display screen of the display.

9. The ultrasound diagnostic imaging apparatus of claim 1, wherein, when an operation of sliding from a center to an edge section is detected in an ultrasound display region with an ultrasound image in the selected state, the processor advances a display mode to a single display mode to display one ultrasound image on the display screen of the display.

10. The ultrasound diagnostic imaging apparatus of claim 1, wherein in the vertical display mode, the two vertical ultrasound display regions have quadrilateral shapes, and wherein in the horizontal display mode, the two horizontal ultrasound display regions have quadrilateral shapes.

* * * * *